(12) United States Patent
Schoedl et al.

(10) Patent No.: US 12,027,271 B2
(45) Date of Patent: Jul. 2, 2024

(54) VISUALIZATION OF BIOMEDICAL PREDICTIONS

(71) Applicant: HOFFMANN-LA ROCHE INC., Little Falls, NJ (US)

(72) Inventors: Thomas Schoedl, Penzberg (DE); Stefanie Kaufmann, Penzberg (DE); Markus Bundschus, Penzberg (DE); Antonia Stank, Penzberg (DE); Marius Rene Garmhausen, Penzberg (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 912 days.

(21) Appl. No.: 17/051,002

(22) PCT Filed: Apr. 30, 2019

(86) PCT No.: PCT/EP2019/061118
§ 371 (c)(1),
(2) Date: Oct. 27, 2020

(87) PCT Pub. No.: WO2019/211308
PCT Pub. Date: Nov. 7, 2019

(65) Prior Publication Data
US 2021/0366618 A1    Nov. 25, 2021

(30) Foreign Application Priority Data

May 3, 2018    (EP) ..................................... 18170624

(51) Int. Cl.
*G16H 50/30*    (2018.01)
*G16H 50/70*    (2018.01)
(52) U.S. Cl.
CPC ............. *G16H 50/30* (2018.01); *G16H 50/70* (2018.01)

(58) Field of Classification Search
CPC ......... G16H 50/30; G16H 50/70; G16H 50/20
See application file for complete search history.

(56) References Cited

U.S. PATENT DOCUMENTS

| 5,485,600 A | 1/1996 | Joseph et al. |
| 2006/0129326 A1 | 6/2006 | Braconnier et al. |

(Continued)

FOREIGN PATENT DOCUMENTS

| CN | 102822834 A | 12/2012 |
| CN | 104424074 A | 3/2015 |

(Continued)

OTHER PUBLICATIONS

Ja DiMasi et al., "A Tool for Predicting Regulatory Approval After Phase II Testing of New Oncology Compounds", Aug. 2015, wileyonlinelibrary.com, Clinical Pharmacology & Therapeutics, vol. 98 No. 5, pp. 506-513. (Year: 2015).*

(Continued)

*Primary Examiner* — Daniel W Parcher
(74) *Attorney, Agent, or Firm* — Harness, Dickey & Pierce, P.L.C.

(57) ABSTRACT

The mobile device receives a prediction result via a digital cellular mobile telecommunication network. The prediction result has been generated by a program logic using a biomedical model. The prediction result includes a prediction score, a first confidence interval of prediction scores known to have a percentage of false negative predictions below a predefined FN-percentage threshold and a second confidence interval of score values known to have a percentage of false positive predictions below a predefined FP-percentage threshold. The mobile device displays an analog scale icon including a background area having the prediction score, an analog scale representing the score range; a pointer; a first sub-range indicator indicating the size and position of the first confidence interval; and a (Continued)

second sub-range indicator indicating the size and position of the second confidence interval within the score range.

17 Claims, 7 Drawing Sheets
(6 of 7 Drawing Sheet(s) Filed in Color)

(56) References Cited

U.S. PATENT DOCUMENTS

| | | | |
|---|---|---|---|
| 2007/0168231 A1 | 7/2007 | Sasai | |
| 2010/0131883 A1* | 5/2010 | Linthicum | G16H 40/63 |
| | | | 715/771 |
| 2011/0077968 A1* | 3/2011 | Kelly | G16H 15/00 |
| | | | 705/2 |
| 2011/0125038 A1 | 5/2011 | Cotter et al. | |
| 2013/0246960 A1* | 9/2013 | Saylors | G16H 15/00 |
| | | | 715/771 |
| 2014/0214454 A1* | 7/2014 | Kahn | G16H 20/30 |
| | | | 705/3 |
| 2014/0267299 A1* | 9/2014 | Couse | G06T 11/206 |
| | | | 345/440.2 |
| 2015/0046137 A1 | 2/2015 | Zeilinger | |
| 2015/0169838 A1* | 6/2015 | Simon | G16Z 99/00 |
| | | | 702/19 |
| 2015/0227299 A1 | 8/2015 | Pourshahid | |
| 2018/0060512 A1* | 3/2018 | Sorenson | G06Q 10/06398 |

FOREIGN PATENT DOCUMENTS

| | | |
|---|---|---|
| CN | 107621849 A | 1/2018 |
| JP | 2014-199392 A | 10/2014 |
| JP | 2016-532935 A | 10/2016 |
| WO | WO-2006/089970 A1 | 8/2006 |
| WO | WO-2017/091736 A1 | 6/2017 |
| WO | WO-2017/194431 A1 | 11/2017 |
| WO | WO-2018/073646 A1 | 4/2018 |

OTHER PUBLICATIONS

Brian Burton, "How Much is Enough—An Intro to Monte Carlo Simulations", Jun. 6, 2017, ballastplan.com, https://ballastplan.com/how-much-is-enough-an-intro-to-monte-carlo-simulations/, pp. 1-4. (Year: 2017).*

International Search Report PCT/ISA/210 for International Application No. PCT/EP2019/061118 Dated Jul. 5, 2019.

Written Opinion of the International Searching Authority PCT/ISA/237 for International Application No. PCT/EP2019/061118 Dated Jul. 5, 2019.

Gayvert Kaitlyn M et al., "A Data-Driven Approach to Predicting Successes and Failures of Clinical Trials", Cell Chemical Biology, Elsevier, Amsterdam, NL, vol. 23, No. 10, Sep. 15, 2016 (Sep. 15, 2016), p. 1294-1301.

Stefan Wager et al., "Confidence Intervals for Random Forests: The Jackknife and the Infinitesimal Jackknife," Journal of Machine Learning Research 15, 2014, pp. 1625-1651.

Abshul Kundaje et al., "A Classification-based Framework for Predicting and Analyzing Gene Regulatory Response," BMC Bioinformantics 2006, pp. 1-14.

Decision to Grant Patent, dated Jun. 6, 2023, issued in corresponding Japanese Patent Application No. 2020-559413.

Chinese Office Action, dated Jun. 29, 2023, issued in corresponding Chinese Patent Application No. 201980030113.7.

International Preliminary Report on Patentability and Written Opinion for PCT/EP2019/061118 dated Nov. 12, 2020.

Office Action for European Application No. 19 720 620.4 dated Aug. 25, 2022.

Anonymous: "Biomedical model—Wikipedia," Oct. 21, 2021 (Oct. 21, 2021), XP55953131, Retrieved from the Internet: URL:https://en.wikipedia.org/wiki/Biomedical_model [retrieved on Aug. 19, 2022].

* cited by examiner

Ranking of prediction results

| Target | Indication | Score | Prediction | Project-Type | Drug-Type | Article Count | Score Visualization | |
|---|---|---|---|---|---|---|---|---|
| | | 0.69 | Positive outcome | New molecular entity | Biological | 548 | | 304 Detail |
| | | 0.39 | Negative outcome | New molecular entity | Biological | 73 | | 306 Detail |

Fig. 3

VISUALIZATION OF BIOMEDICAL PREDICTIONS

CROSS-REFERENCE TO RELATED APPLICATIONS

This application is a national phase under 35 U.S.C. § 371 of PCT International Application No. PCT/EP2019/061118 which has an International filing date of Apr. 30, 2019, which claims priority to European Patent Application No. 18170624.3, filed May 3, 2018, the entire contents of each of which are hereby incorporated by reference.

FIELD OF THE INVENTION

The invention relates to the field of model-based biomedical predictions, and more particular to model-based biomedical predictions visualized by matrix displays of mobile devices.

BACKGROUND AND RELATED ART

Predictive modeling in the biomedical domain faces multiple pressing problems: scientists and health care managers need to make use of a growing number of model based predictors for all kinds of biomedical predictive tasks. For example, neural networks or support vector machines may be used for predicting the best suited cancer therapy for a patient, for identifying suitable epitopes within a protein sequence, for identifying particular patterns in a DNA sequence, for identifying drug target candidates in a molecular library or for predicting the 3D structure of a protein. Statistical models and data derived from patient cohorts are used for predicting whether a particular drug showed an improved effect compared to the drug used in the standard treatment or whether the drug shows an effect at all. The great diversity of the predictive models is accompanied by a corresponding diversity of user interfaces. Often, only a small fraction of the information that is originally generated by a predictive model is actually displayed to the user. However, if a user is only presented a binary "yes or no" result, valuable information on the certainty (i.e., reliability) of this prediction and/or on the accuracy of the model the prediction is based on may get lost. Loss of context information in the context of biomedical prediction is a pressing problem in the biomedical domain in which the data, the models and the patients often are characterized by unique combinations of features and conditions and by "grey value states", i.e., states which do not allow a clear cut decision if a patient/cell/tissue has a particular feature or not.

On the other hand, if a user interface of a predictive model outputs all the context information that may be available, this interface is not suited for use with hand held mobile devices because the small screen imposes a limitation on the complexity of data that can be displayed. Furthermore, it is not possible to display the results of multiple model based predictions on a single screen without losing important context information. Nevertheless, frequent traveling between different working places, customers, hospitals, universities and congress centers has meanwhile become an integral component of the daily working routine of many scientists and health care providers which use their mobile phones for performing their work.

A further problem is the rapid speed of information gain in the biomedical domain, so predictive models soon become outdated.

Kundaje A, Middendorf M, Shah M, Wiggins CH, Freund Y, Leslie C. in "A classification-based framework for predicting and analyzing gene regulatory response", BMC Bioinformatics. 2006;7(Suppl 1):55. doi:10.1186/1471-2105-7-S1-S5describe a prediction framework in the biomedical domain that visualizes the prediction result in the form of a combination of a scatter plot and a confusion matrix. The scatter plot is a particular, model-specific form of visualizing the result and the confusion matrix provides some information on the quality of the model. However, even experts often do not understand the information conveyed by a confusion matrix. Moreover, it is very hard, or even impossible, to provide the information contained in the plot and the matrix on a small screen of a mobile phone, and the output cannot be compared with other predictions of the same or other models easily.

US patent application US 2006/129326 A1 describes a method for improved control of clinical trials. After a clinical trial is initiated, data is regularly cleaned and processed to statistically analyze the data. The outcome includes a predictive measure of the timing and level by which the study will achieve one or more statistically significant levels, allowing mid-course modifications to the study. Gayvert Kaitlyn M. et al. in "A Data-Driven Approach to Predicting Successes and Failures of Clinical Trials", CELL CHEMICAL BIOLOGY , ELSEVIER, AMSTERDAM, NL, vol. 23, no. 10, 15 Sep. 2016, pages 1294-1301, XP029774258, describes the problem that the number of clinical trial failures has risen substantially in the last years. It is difficult to identify compounds that have unfavorable toxicity properties before conducting clinical trials. The authors suggest a "moneyball" approach that analyzes overlooked features to predict clinical toxicity. A new data-driven approach (PrOCTOR) directly predicts the likelihood of toxicity in clinical trials.

SUMMARY

It is an objective of the present invention to provide for an improved method of visualizing the certainty of a model-based prediction on a matrix display of a battery powered hand held mobile device and a corresponding mobile device as specified in the independent claims. Embodiments of the invention are given in the dependent claims. Embodiments of the present invention can be freely combined with each other if they are not mutually exclusive.

In one aspect, the invention relates to a method of visualizing the certainty of a biomedical model-based prediction on a matrix display of a battery powered hand held mobile telecommunication device. The method comprises receiving, by the mobile device, a prediction result via a digital cellular mobile telecommunication network. The prediction result has been generated for a biomedical prediction task by a program logic using a biomedical model. The prediction result comprises at least a prediction score, a first confidence interval and a second confidence interval.

The prediction score is indicative of the certainty of the prediction and is a numerical value within a score range. The score range is a predefined range of possible score values. Preferably, the prediction score is a normalized prediction score and the predefined score range is a numerical score range, e.g. a score range between −1 and +1 or between 0 and 1.

The goal of the prediction can be, for example, to assess the membership of a particular object in one of two classes (i.e., to perform a binary classification of an object either into class "C0" or into class "C1"). Each of the two classes is represented by one of the two borders of the possible score value range, e.g. "0" and "1" for a score value range [0, 1] or "−1" and "+1" for a score value range [−1, +1]. The prediction score indicates how secure (reliable) this assessed membership is. "Ideal" (absolutely reliable) score values would always be the maximum or minimum possible score value in the score value range. For example, the "ideal" score would either be 0 or 1 (if the possible score value range is [0-1]) or would be −1 or 1 (if the possible score value range is [−1 to +1]). The farther away the computed prediction score value from the nearest one of the two score range borders (i.e., the closer the score is to 0.5 in the context of the range [0-1] or the closer to 0 in the context of the range −1 to +1), the more insecure is the predicted membership represented by said nearest score range border. For example, the class C0 could represent the prediction result: "this drug will be approved by the FDA for treating a particular disease", and the class C1 could represent the prediction result: "this drug will not be approved by the FDA to treat this particular disease".

The first confidence interval is a first sub-interval of the score range. The first confidence interval is indicative of the model-specific sub-range of score values known to have a percentage of false negative (FN) predictions below a predefined FN-percentage threshold.

The second confidence interval is a second sub-interval of the score range. The second confidence interval is indicative of the model-specific sub-range of score values known to have a percentage of false positive (FP) predictions below a predefined FP-percentage threshold.

The method further comprises displaying, by the mobile device, an analog scale icon on a matrix display of the mobile device. The analog scale icon comprises a background area comprising the prediction score. The analog scale icon further comprises an analog scale, a pointer, a first sub-range indicator and a second sub-range indicator.

The analog scale represents the score range. The ends of the scale represent the maximum and minimum score values of the score range.

The pointer points towards a location within the scale that represents the prediction score.

The first sub-range indicator being aligned with the scale such that the size and position of the first sub-range indicator relative to the scale is indicative of the size and position of the first confidence interval within the score range.

The second sub-range indicator being aligned with the scale such that the size and position of the second sub-range indicator relative to the scale is indicative of the size and position of the second confidence interval within the score range.

Said features may be advantageous, because the analog scale icon may allow any user to immediately and intuitively understand the outcome of the prediction as well as the quality and certainty of the prediction and of the accuracy of the model the prediction is based on without involving a conscious reading, understanding and interpretation of any numerical value or value range: a score value is a numerical value that cannot be interpreted intuitively due to limitations of human physiology. Furthermore, the understanding of the score value is hampered by lack of experience and expert knowledge in the technical field of machine learning. In order to overcome the physiologic limitation of human perception of numerical values, and in order to fully understand the meaning of a score value and how reliable the score value is, a user was previously forced to consciously read the numerical score value, consciously memorize the scale of possible score values, compare the score value with this range and decide if the prediction result should be interpreted as a confirmation or rejection of a particular hypothesis. Moreover, in order to assess the accuracy of the model used for performing the prediction, the user previously had to navigate to other pages or display regions comprising further numerical values indicating the quality of the model, read the numerical values, understand them and interpret the prediction result in view of this additional information.

To the contrary, by providing an analog scale and a pointer pointing to the prediction score value within this scale provides for a visualization of the prediction result that can be quickly and intuitively understood without involving a conscious reading, understanding and interpretation of numerical values or value ranges. Thus, the understanding of the information conveyed in the analog scale icon does not depend on psychological or other subjective factors but on the relative position of a pointer, a scale and two sub-range indicators aligned with the scale. The relative positioning of objects represents a form of data representation which can quickly be processed given the physiology of human brains evolved over million years in a world full of moving objects whose quick interpretation was often key for survival.

In a further beneficial aspect, the information encoded in the model prediction result is presented such that it can also be recognized and intuitively understand if presented on a small screen. Even in case the screen is too small to allow a user to read and recognize the numerical value encoded in the scale and the prediction score, and even in case the scale does not comprise any scale values at all, the user may still intuitively assess the prediction result simply based on the direction of the pointer relative to the analog scale. In case the display allows presenting numerical values that are big enough to be human-readable, the visualization in form of the analog scale still improves the readability of the numerical values, because the pointer provides intuitively recognizable information that may allow a user to immediately recognize that a numerical number wrongly perceived to be "0.7" at first glance is in fact a "0.1", because the pointer may point to a low numerical value close to the median value of the scale (e.g. 0) rather to a high numerical value close to the maximum value of the scale (e.g. 1).

In a further beneficial aspect, the analog scale icon comprises first and second sub-range indicators which are indicative of scale regions representing prediction score values which are considered as particularly reliable, because in these sub-ranges only a very low fraction of false positive and false negative prediction results are expected. These sub-ranges are model specific and the width of the sub-ranges may differ for false positive results and false negative results. Thus, the width of the first and second sub-range informs the user on the quality of the model (in general and irrespective of the quality and certainty of the present prediction result).

For example, in the predictions computed based on a particular model, the score value "0" represents the event (classification result) "negative" and score value 1 represents the event (classification result) "positive", which is usual. The score value "0" may represent a first class "C0" and define the lower border of the first confidence interval. The score value "1" may represent a second class "C1" and define the upper border of the second confidence interval.

In case the score values are normalized between −1 and +1 rather than between 0 and 1, the score value "−1" may represent a first class "C0" and define the lower border of the first confidence interval. The score value "+1" may represent a second class "C1" and define the upper border of the second confidence interval.

According to a further example, a user may receive a prediction score of 0.7 based on a model M1. This score is a highly reliable prediction result because the second sub-range of model M1 covers a range from 0.6 to 1.0 and means that the risk of a false positive prediction result is below 10% if the score value is at or above 0.6. The high quality of the model M1 in respect to false positive results can quickly and intuitively be comprehended by the user, because the second sub-range is quite large. The high quality of the prediction can be assessed intuitively because the pointer points to a location in the scale that is aligned to and covered by the second sub-range indicator. Then, the user may receive a prediction score of 0.7 based on a different model M2. This score is not a reliable prediction result because the second sub-range of model M2 covers a range from 0.9 to 1.0 and means that the risk of a false positive prediction result is below 10% if the score value is at or above 0.9. The low quality of the model M2 in respect to false positive results can quickly and intuitively be comprehended by the user, because the second sub-range is quite small. The low quality of the prediction can be assessed intuitively because the pointer points to a location in the scale that is not aligned to and is not covered by the second sub-range indicator.

In a further beneficial aspect, the analog scale icon may provide sufficient context information to allow a user to assess both the quality of the particular prediction result received and also the quality of the model used for the prediction, whereby the analog scale icon can be displayed on a small matrix display of a hand-held, portable mobile device. Thus, a user does not have to scroll or otherwise navigate to additional GUI panes or pages comprising additional model-related information such as confusion matrices, statistical quality parameters of the models, or the like. Rather, the analog scale icon may provide, in a single condensed (compressed) view, the prediction result and context information allowing a skilled user to intuitively assess the quality and certainty of the individual prediction as well as of the quality and accuracy of the model in general. The visualization can be applied for the output of any biomedical model that generates a prediction score and for which score ranges are known within which the share of false positive or false negative predictions is below a predefined threshold range, e.g. below 10%, or below 5%. Thus, the predictions of many different biomedical models or of many different versions of the same models can be visualized and compared with each other easily and intuitively.

According to some examples, the method is executed as a sub-routine within a semi-automated process of deciding whether or not research on a particular drug should be continued or not which again depends on the likelihood that the drug will later be approved by an authority for treating a particular disease. Alternatively, the analog scale icon may be used for predicting if a particular protein sequence is a good epitope candidate, is a binding domain for another molecule, or the like, whereby in dependence on the prediction result, further computational or wet-lab steps are performed for analyzing a drug, a protein, or any other biomedical object. Thus, the representation of a prediction result in the form of an analog scale icon may accelerate a guided human-machine interaction process.

According to some embodiments, the analog scale icon is a speedometer icon.

According to some embodiments, the background area is a tacho disc area.

According to some embodiments, the scale is a part of the outline of the background area.

According to some embodiments, the pointer originates at the center of the background area.

According to some embodiments, the background area is a semicircle.

According to some embodiments, the first and second sub-range indicators respectively are a segment arc, in particular a circle segment arc.

According to some embodiments, the prediction score is displayed at the center of the background area.

According to some embodiments, the analog scale icon further comprises a center area concentrically aligned with the background area. The center area displays the score value.

According to embodiments, the prediction result further comprises a prediction-variance-interval. The prediction-variance-interval is indicative of a sub-range of the score range. The width of the prediction-variance-interval negatively correlates with the robustness of the model and the model-based prediction against small variations in the input data used for computing said prediction.

Hence, the prediction-variance-interval is a type of estimate of the robustness of the predictions generated by the model against small variations in the input data used for computing the prediction. Ideally, small variations in the input data should only result in small variations of the prediction result indicated by the score value.

The analog scale icon further comprises a variance bar arranged perpendicular to the pointer. The width of the variance bar correlates with and is indicative of the width of the prediction-variance-interval. The variance bar is preferably arranged such that its center covers the center of the axis of the pointer.

In general, the variance bar describes the variance (e.g. the standard deviation) of the prediction score. The variance bar indicates the impact of small variations in the input data used for a particular prediction on the score value. An ideal/highly certain prediction can quickly identified by the user by determining that the pointer indicating the score value of the prediction lies within the range of one of the confidence intervals and is associated with a variance bar that is completely within the range of the confidence interval. Thus, complex information relating to the certainty of a model-based prediction can be perceived by a user quickly and intuitively.

Said features may be advantageous, because while the direction of the pointer relative to the scale indicates the result of the prediction, the width of the variance bar provides additional information on the "certainty" of this particular prediction. The wider/larger the variance bar, the wider the angle of possible pointer directions which are covered by the variance bar. A wide/large variance bar indicates that the trained model is very sensitive to small variations in the model training data and thus that also the current prediction score (the direction of the pointer) is not very robust against minor variations in the input data. In other words, a wide/large variance bar indicates that the current prediction is not very reliable and is not very robust.

For example, in response to a first prediction request of a user, a first prediction result with a prediction score of 0.7 and a short prediction variance bar, indicating a small range of variability of the score along the area of the scale (e.g. ranging from 0.69 to 0.71), is generated and displayed. The score value and the direction of the pointer may indicate that a hypothesis like "drug X will be approved by FDA for treating disease D" is predicted to be true with a score value of 0.7. The range 0.69 to 0.71 may be computed based on a user-defined or otherwise defined prediction-confidence-level, e.g. 95%. The pointer may be covered by a short variance bar representing and indicating the width of 0.02 score units. The user immediately and intuitively comprehends that the certainty of this particular result is very high, because the variance bar is short.

In contrast, in response to a second prediction request of the user, a second prediction result with a prediction score of 0.7 and a long variance bar, indicating a large range of variability of the score along the area of the scale (e.g. ranging from 0.5 to 0.9), is generated and displayed. Like in the first example, the score value and the direction of the pointer may indicate that a hypothesis like "drug X will be approved by FDA for treating disease D" is predicted to be true with a score value of 0.7. The range 0.5 to 0.9 may also be computed based on the above mentioned prediction-confidence-level, e.g. 95%. The pointer may be covered by a broad variance bar representing and indicating the width of 0.4 score units. In this case, the user can easily comprehend that the certainty of this particular score is significantly lower because the variance bar of the second prediction is larger than the variance bar of the first prediction. A large variance bar indicates that small changes in the input parameter value may have a large impact on the computed prediction score and/or may indicate that a re-training of the model-based predictor based on a slightly different training data set may have a large impact on the computed prediction score for the currently used input data.

The "prediction-variance-interval" as used herein is a measure that is used to quantify the amount of variation or dispersion of a set of prediction scores computed by a model-based prediction logic. A small prediction-variance-interval indicates a small amount of dispersion, a large prediction-variance-interval indicates a large amount of dispersion.

For example, the training data used for generating and training the model-based predictor can be a training data set obtained by data sampling from a super-set of training data. Data sampling is a technique to select a subset of the training set at each epoch. This could be a way to make the epoch unit smaller or select relevant training sequences at each epoch. This is also often performed when working on very large datasets—where the full data does not need to be loaded in memory for each epoch. Hence, the "prediction-variance-interval" according to embodiments of the invention gives an estimate of the sampling variance of the super-set training data; in other words, the prediction-variance-interval indicates how much the prediction scores computed by a particular model-based machine learning logic might change if it was trained on a new training set sample.

Typically, if the training data that was originally used for training the model-based prediction logic was a large, high quality training data, i.e., comprises a sufficient amount of true positives and true negatives, is free of larger biases and accurately represents the composition of the "real world", the prediction score computed by the model-based predictor will probably be robust against small variations in the training data set. For example, the training set used for training a model-based prediction logic may be a sampled training set and the prediction-variance-interval according to embodiments of the invention gives an estimate of the sampling variance of the random forest; in other words, the prediction-variance-interval indicates how much the predictions of a model-based prediction logic, e.g. a neural network or random forest's prediction logic, might change if it would be trained it on a new training set. Typically, the width of the prediction-variance-interval of a prediction generated by a MLL being a bagged learner depends and is indicative of the variance of the base learner.

According to embodiments, the width of the variance bar is identical to the chord length of a visible or non-visible circle segment. Said circle segment originates at the center of the background area. The two ends of the variance bar intersect with the legs of the circle segment. The arc of the circle segment is a part of the scale that corresponds to the prediction-variance-interval.

According to embodiments, the method further comprises automatically generating, by the program logic using the biomedical model, the prediction result.

According to embodiments, the program logic is installed on a server computer system. The method further comprises: automatically generating, by the program logic using the biomedical model, the prediction result; and sending the prediction logic to the mobile device via a network. Alternatively, the method comprises sending a message to the mobile device via a network, the message notifying the mobile device that the prediction result was generated, and downloading the prediction result by the mobile device from the server computer.

According to embodiments, the program logic is a trained machine-learning logic.

According to embodiments, the method further comprises repeatedly receiving training data. Each received training data update comprises at least some data not being contained in the previously received training data. Upon each receipt of training data, the method comprises automatically re-training the machine learning logic on the currently received training data, thereby automatically generating an updated version of the biomedical model.

This may be advantageous, because the amount of data and knowledge available in many fields of biology and medicine rapidly increases. Thus, a prediction result may rapidly become outdated. By automatically re-training the machine learning logic on newly available information and automatically triggering a re-computation of the prediction result based on updated versions of the biomedical models, it can be ensured that scientists and management staff in the biomedical domain can decide based on predictions provided by up-to-date biomedical models.

According to embodiments, the biomedical model used by the machine learning logic is a first biomedical model having been generated based on first training data. The mobile device is one of a plurality of mobile devices respectively assigned to one of a plurality of users. The method further comprises registering the plurality of users and a plurality of biomedical prediction tasks at a backend program. For example, the backend program may maintain and manage a user- and prediction task registry. Each registered user has assigned one or more of the prediction tasks. The machine learning logic performs each of the prediction tasks, thereby respectively using the first biomedical model for generating a first prediction result. The method comprises sending the first prediction results selectively to the mobile devices of the users to which the prediction tasks for which the first prediction results were generated are assigned. In response to each re-training of the machine learning logic, the machine learning logic automatically performs each of the prediction tasks a further time, thereby respectively using the updated version of the biomedical model for generating a second prediction result. Then, the method comprises sending the second prediction results or a notification of their computation selectively to the mobile devices of the users to which the prediction tasks for which the first prediction results were generated are assigned.

According to some embodiments, the prediction tasks are executed based on many different types of models, e.g. literature-based models, microarray-data based models, and the like. The user and task registry further comprises an assignment of prediction tasks and model-IDs and the background program is configured to select for each prediction task to be performed or re-performed the appropriate model based on the model-ID and task assignment in the registry.

This may be advantageous, because on the one hand it is ensured that a plurality of users are always provided with the latest available prediction results for an arbitrary number of different prediction tasks. At the same time, network traffic is avoided, because only those users which have registered for a prediction task for which a model-update was performed are notified of a prediction result.

According to some embodiments, the backend program compares the first prediction result and the second prediction result computed for each prediction task. The sending of the second prediction results or the sending of the notification of their computation is performed selectively for those prediction tasks for which a first prediction result and a second prediction result were computed which fulfill one or more of the following conditions:

- the score value of the second prediction result but not the score value of the first prediction result lies within the first confidence interval; for example, this may mean that the new prediction result is observed to have entered a score range considered to be particularly reliably due to a low portion of FNs (e.g. a ratio of <10% FNs); or
- the score value of the first prediction result but not the score value of the second prediction result lies within the first confidence interval; for example, this may mean that the new prediction result is observed to have suddenly entered a score area considered to be non-reliable due to many FNs (e.g. a ratio of >10% FNs); or
- the score value of the first prediction result but not the score value of the second prediction result lies within the second confidence interval; for example, this may mean that the new prediction result is observed to have suddenly left a score area considered to be particularly reliable due to a low portion of FPs (e.g. a ratio of <10% FPs); or
- the score value of the second prediction result but not the score value of the first prediction result lies within the second confidence interval; for example, this may mean that the new prediction result is observed to have suddenly entered a score area considered to be particularly reliable due to a low ratio of FPs (e.g. a ratio of <10% FPs); or
- the score value of the first and second prediction result differ by more than a predefined score difference threshold; for example, this may mean that the model-based prediction suddenly improves or deteriorates significantly; or
- the size of the prediction-variance-interval of the first and second prediction result differ by more than a predefined interval length difference threshold. For example, this may mean that the quality of the model-based prediction suddenly improves or deteriorates significantly, e.g. due to changed variability of the training data.

This may help avoiding network traffic and unnecessarily disturbing the registered users, because a user is notified of a prediction result only in case the prediction result generated based on the updated model is significantly different from the prediction result generated based on the previous model version and/or only in case the certainty of the model or the certainty of the prediction result generated based on the updated model is significantly different from the certainty of the model or the certainty of the prediction result generated based on the previous model version.

According to embodiments, the machine learning logic has been trained on biomedical literature. The machine learning logic is adapted to predict the likelihood of failure of a pre-clinical or clinical trial examining the treatability of a particular disease by a particular drug using features automatically extracted from the biomedical literature.

According to embodiments, the mobile device receives a plurality of prediction results comprising the prediction result. Each of the received prediction results has been generated by the program logic using the biomedical model on different input data. For example, the prediction logic may be used for predicting whether a particular drug D1 having a target molecule T1 will be approved by the FDA for treating disease D and may in addition be used for prediction whether a particular drug D2 having a target molecule T2 will be approved by the FDA for treating the disease D. Thus, the input data for the two predictions may differ because the names of the drug targets T1, T2 differ. The mobile device displays a prediction list on the display of the mobile device. Each list item represents one of the received prediction results and comprises at least a thumbnail-analog scale icon graphically representing said prediction result. Each thumbnail-analog scale icon comprises at least a size-reduced version of the scale, a size-reduced version of the background area with the prediction score, and a size-reduced version of the pointer originating at the center of the size-reduced background area and pointing towards a location within the size-reduced scale that represents the prediction score. Upon a user's selection of one of the list items, the generation and the displaying of the analog scale icon is performed, wherein the displayed analog scale icon represents the prediction result represented by the selected list item. The displaying is performed such that the analog scale icon replaces the prediction list on the matrix display of the mobile device.

This may be advantageous, as already the thumbnail analog scale icons may provide a user with an intuitive impression of the prediction result and the quality of the model used for the prediction. The user is enabled to manage technical task, such as comparing and interpreting a plurality of biomedical prediction results generated by one or many models or model versions, in a more efficient and accurate manner.

Embodiments of the invention may allow identifying the most appropriate target and, in general, to compare and evaluate different use case and data input scenarios to find the best solution for a particular biomedical task, e.g. the task of identifying a drug and/or a drug target. In this case, the same model is used for performing the predictions.

In a further beneficial aspect, embodiments of the invention may allow comparing the predictions of different models.

The prediction results in the list comprising the thumbnail analog scale images enable the user to quickly identify model predictions which differ significantly from the prediction results provided by other models or other versions of the same model and/or to quickly identify a prediction being based on a model or model version of particular high or low quality or accuracy. Thus, an interface is provided that may allow a user to quickly and intuitively comprehend the accuracy of different versions of the same model and also to identify trends in the development of this model and its accuracy if repeatedly trained on an training data set of growing size. This may be particularly advantageous in the context of biomedical research where the amount of data increases rapidly and thus the quality of many predictive models can be increased by repeatedly training the model on an updated version of the training data. This may allow comparing and evaluating different input scenarios and model versions and may allow identifying the best model and model version for performing a predictive task. The identification of said prediction results within a large list of prediction results by comparing thumbnail analog scale images does not depend on subjective psychological traits of an individual user. Rather, the interpretation of analog information is faster than the interpretation of numerical values or value ranges in all human beings due to physiological properties of the human brain.

According to embodiments, the analog scale icon is displayed as an element of a graphical user interface that is free of a scroll bar and/or that does not support scrolling.

This may be advantageous as the scrolling operation consumes a large amount of energy and processing power and the scrolling may no longer be necessary because all relevant information for interpreting the result of a prediction by a scientist are visualized in the analog scale icon.

According to embodiments, the generation of the analog scale icon is performed by a browser executing a script element of a web page provided by a server computer.

According to other embodiments, the generation of the analog scale icon is performed by a browser plug in of a browser displaying a web page provided by a server computer.

According to other embodiments, the generation of the analog scale icon is performed by an application program ("app"). The application program is interoperable with a backend program hosted by the server computer. The backend program is adapted to provide the prediction result to the mobile device via a network.

According to embodiments, the method further comprises normalizing an original prediction score generated by the program logic and using the normalized prediction score as the prediction score generated by the program logic. The normalized score is normalized based on a predefined score range.

According to embodiments, the method further comprises repeatedly performing, by the program logic, the generation of the prediction result for the biomedical prediction task, thereby using repeatedly updated versions of the biomedical model. The method further comprises visualizing the change of the accuracy of the repeatedly updated biomedical model in the form of a moving image of the analog scale icon, wherein the size of the first and second sub-range indicators, the direction of the pointer and/or the size of the variance bar, if any, vary in the moving image over time.

Generating moving-images from a sequence of analog scale icons may be particularly beneficial, because it is physiologically not possible for a human being to understand intuitively the development of five numerical values (the score value and the two ends of each sub-range interval) over time. This is because the human brain is not able to read, interpret and analyze five numerical values in parallel, in particular in case these values change dynamically over time. To the contrary, the physiology of the human brain allows intuitively understanding and interpreting the movement of a pointer along a static scale and the increase or decrease of two range indicators over the time. Thus, the use of analog scale icons allows visualizing trends regarding the quality of prediction as well as the quality of the model itself over time, thereby allowing a user to process and understand more information at a time than possible if the results and model qualities would be presented based on numerical values and value ranges.

In a further aspect, the invention relates to a mobile hand-held telecommunication device comprising a battery for powering the mobile device, a digital cellular network interface, a matrix display and a program logic (also referred to as "client side program logic"). The program logic can be, for example, a client application program, e.g. a stand-alone application program or a browser-plug-in, or a script, e.g. a JavaScript code embedded in a web page. The program logic is executable by the one or more processors of the mobile device and is configured for receiving a prediction result via the digital cellular network interface. The prediction result has been generated for a biomedical prediction task by a prediction program logic using a biomedical model. The prediction result comprises at least a prediction score, a first confidence interval, and a second confidence interval.

The prediction score is indicative of the certainty of the prediction and being a numerical value within a score range, the score range being a predefined range of possible score values. Preferably, the score value is a normalized score value and the score value range is a range of normalized score values.

The particular way of computing a score may depend on the mathematical model used. For example, in case the model is a RandomForest model, the prediction score quantifies the RandomForest model's certainty by calculation of the percentage of decision trees in the RandomForest that have come to the conclusion that the sample belongs to class C1. It is calculated as follows: score=sum(DT where O(DT)=C1)/sum(DT) with DT=Decision trees, O is a function describing the output of a decision tree and C1 being the positive class.

The first confidence interval is a first sub-interval of the score range. The first confidence interval is indicative of the model-specific sub-range of score values known to have a percentage of false negative predictions below a predefined FN-percentage threshold.

The second confidence interval is a second sub-interval of the score range. The second confidence interval is indicative of the model-specific sub-range of score values known to have a percentage of false positive predictions below a predefined FP-percentage threshold.

The client side program logic is further configured for displaying an analog scale icon on the matrix display. The analog scale icon comprises a background area comprising the prediction score, an analog scale, a pointer, a first sub-range indicator and a second sub-range indicator. The analog scale represents the score range, whereby the ends of the scale represent the maximum and minimum score values of the score range. The pointer points towards a location within the scale that represents the prediction score. The first sub-range indicator is aligned with the scale such that the size and position of the first sub-range indicator relative to the scale is indicative of the size and position of the first confidence interval within the score range. The second sub-range indicator is aligned with the scale such that the size and position of the second sub-range indicator relative to the scale is indicative of the size and position of the second confidence interval within the score range.

In a further aspect, the invention relates to a system comprising the mobile device and a server computer. The server computer can be connected to the mobile device via a network connection established via the cellular network interface. The server computer comprises the biomedical model, the predictive program logic configured to use the biomedical model for generating the prediction result, and a backend program adapted to provide the prediction result via a network to the mobile device.

The system can optionally comprise a plurality of further mobile devices of further users who may have registered at a user- and task registry managed by a remote program logic hosted on the server computer.

A "training data set" or "training data" as used herein is a set of data records, e.g. tissue images, electronic documents, micro array data, protein expression profiles, etc. that comprises manually or automatically annotated meta data allowing the MLL to learn, based on the training data, a predictive model that incorporates biomedical knowledge contained in the training data and that can be used for performing a prediction for a biomedical question. The training data are used for training an untrained version of the MLL for generating a trained MLL that is adapted to perform a particular prediction task. For example, the training data set can comprise electronic documents wherein the name of a disease and the name of a target molecule of a particular drug assumed to be of use for treating the disease were both mentioned and may comprise several features extracted from said documents, e.g. author names, publication date, journal impact factor, and the like. The electronic documents in the training data set are annotated with a flag indicating whether the drug was approved by the FDA for treating the disease or was rejected by the FDA or failed for other reasons during the pre-clinical and clinical trial period. Thus, a MLL may learn from the features contained in the training data set (such as article count, author-networks and the like) to distinguish between a promising drug candidate and a less promising drug candidate based on available biomedical literature and on the features extracted therefrom. A "machine learning logic (MLL)" as used herein is a program logic, e.g. a piece of software, that has been trained or that can be trained in a training process, whereby during the training process, the MLL learns how to perform a prediction for solving a particular predictive tasks from a training data set. For example, the MLL can be a neuronal network or a support vector machine or the like. Thus, an MLL program code may comprise instructions and program routines which are not explicitly specified by a programmer, but which are implicitly learned in a data-driven learning process from the training data. The learning may comprise generating one or more implicit or explicit predictive models that are used by the trained MLL for performing the prediction based on future input data. Machine learning may employ supervised or unsupervised learning.

A "biological model" as used herein is a description of a static or dynamic biological system, including a biomedical system, that is represented in electronic form. For example, the biological model can be a description of a particular substance and of the way this substance interacts with other substances or biomedical mechanisms. The model can be, for example and without limitation, a mathematical, statistical, heuristic or rule-based specification of the biological system. The model can be specified explicitly, as the case e.g. for rule-based biologic models, or can be specified implicitly, e.g. during a training phase of a model based machine learning algorithm. The model can be an integral part of a machine learning based prediction logic. In preferred embodiments, the biological model is a predictive model, i.e., a model for computing a prediction rather than for performing a simulation (as often the case for systems biology models).

A "sub-range indicator" as used herein is a visible GUI element, e.g. a line, an arc, a bar, an arrow or the like that represents the size and position of a sub-range within a super-range. For example, a sub-range indicator can be an arc 202 having a predefined color and thickness and being positioned outside of a background region 220 of an analog scale icon. For example, the sub-range indicator may be aligned with an analog scale 208 that represents the super-range, e.g. the prediction score range, such that the position and size of the sub-range indicator corresponds to the prediction score values in the scale contained within the sub-range.

A "pointer" as used herein is a visible GUI element, e.g. a bar, an arrow, a triangle, a hand or the like. Preferably, the pointer has a long axis and a short axis, whereby the long axis is at least 30%, preferably at least 50% longer than the short axis.

A "prediction score" as used herein is a numerical value that is indicative of a prediction result. For example, the prediction score may be a normalized numerical value. In some examples, in case the normalized prediction score is higher than the median of all possible normalized score values, the prediction result is that a given hypothesis is predicted to be true. In case the normalized prediction score is lower than the median of all possible normalized score values, the prediction result is that a given hypothesis is predicted to be false. Thus, according to embodiments of the invention, the prediction score is a numerical value that indicates which one out of two possible values or classes is likely correct. These two possible values can be, for example: "membership in a particular class: yes or no"; "drug approval by FDA for a particular drug in respect to a particular disease: yes or no"; etc.

A "confidence interval" as used herein is a sub-range within the range of possible score values which indicates that predictions having a score within said sub-range will not have more than a predefined ratio of FP or FN predictions. For example, a first confidence interval can be a first sub-interval of the score range and can be indicative of the model-specific sub-range of score values known to have a percentage of false negative predictions below a predefined FN-percentage threshold, e.g. below 10%. A second confidence interval can be a second sub-interval of the score range and can be indicative of the model-specific sub-range of score values known to have a percentage of false positive predictions below a predefined FP-percentage threshold, e.g. below 10%.

A "prediction-variance-interval" as used herein is a measure that is used to quantify the amount of variation or dispersion of a set of prediction scores computed by a model-based prediction logic. A small prediction-variance-interval indicates a small amount of variation, a large prediction-variance-interval indicates a large amount of variation. Hence, a small prediction-variance-interval (covering only about 7% of the score range or less) may indicate that the score values computed on the currently used input data values and on similar input data values tend to be close to an expected score value. A large prediction-variance-interval indicates that the score values computed on the currently used input data values and on similar input data values tend to be spread out over a wider range of values. The "prediction-variance-interval" can be implemented as a sub-range of score values whereby the width of this sub-range is a measure of the amount of variation or dispersion of the score values.

According to some embodiments, the prediction-variance-interval represents a standard deviation of score values. This may be advantageous as the standard deviation is algebraically simpler than other measures of variance such as the average absolute deviation. However, there are also other measures of the deviation of a prediction score from an expected value, including average absolute deviation, which provide different mathematical properties from standard deviation.

A "confidence-level" or "variation-confidence-level" as used herein is a percentage value. It is used as a basis for computing the prediction-score-interval of a particular prediction. It represents the reliability of the prediction procedure given the particularities of the model-based predictor, e.g. given the size and/or quality of the training data the model-based predictor was trained on.

According to embodiments, the width of the prediction-variance-interval is computed for each prediction by the model-based prediction logic based on a predefined (e.g. user-defined or pre-configured) confidence-level, e.g. a confidence-level of 90%. For example, a prediction-variance-interval generated for a particular prediction based on a confidence-level of 90% and computed by a model-based predictor having been trained on a particular sample of training data is a score interval that fulfills the following condition: "were this prediction to be repeated by numerous other versions of the model-based predictor respectively having been trained on another sample of the training data, the fraction of calculated confidence intervals represented as prediction-variance-intervals (which would differ for each sample) that encompass the true population parameter (the true prediction/classification result) would tend toward 90%.

The higher the confidence-level, the broader the prediction-variance-interval and the variance bar: the prediction-variance-interval computed based on a confidence level of 95% will be smaller than a prediction-variance-interval computed based on a confidence level of 99%.

According to some embodiments, the prediction logic encodes a user interface that enables the user to specify the confidence-level for computing the prediction-variance-intervals, thereby enabling the user to specify the minimum certainty of a prediction that he or she considers acceptable. For example, the confidence-level can be 95%, or 99% or any other percentage value, preferably larger than 90%.

The variability of predictions made by a model-based prediction logic, e.g. bagged learners and random forests, can be determined as described in Stefan Wager, Trevor Hastie and Bradley Efron "Confidence Intervals for Random Forests: The Jackknife and the Infinitesimal Jackknife", Journal of Machine Learning Research 15 (2014) 1625-1651. The variability of a prediction can be expressed, e.g. in the form of a standard error and the width of the prediction-variance-interval can represent and correlate with the standard error.

An "icon" as used herein is a picture that is displayed on a screen, e.g. a matrix display, and that visualizes the result of a model-based prediction and preferably also the certainty of the prediction and/or the accuracy of the model used for generating the prediction. An icon can be implemented in the form of a pixel matrix, a vector graphic or based on a program-language specific library, e.g. the Java Swing or Java awt library. Preferably, any resizing operation of an icon will resize the visual elements contained therein proportionally. An icon is preferably a quickly comprehensible symbol and is more like a traffic sign than a detailed illustration of the actual entity it represents. It can serve as a selectable electronic hyperlink or file shortcut to access additional information related to a particular model-based prediction whose result is graphically visualized by the icon. In this case, the user can select the icon for accessing the additional information using a mouse, pointer, finger, or voice command. According to preferred embodiments, the mobile device is a smartphone or tabloid computer and the icon is selected by a user's finger.

An "analog scale" as used herein is a scale in which information, in particular numerical values like, for example, prediction scores, is encoded in a non-quantized variable, as opposed to a digital scale that encodes information in the form of numbers or characters. For example, many speedometers in old cars are devices with an analog scale encoding the velocity of an object, many "conventional" thermometers are devices with an analog scale encoding the temperature of an object, and so on. An "analog scale icon" is thus an icon that comprises a visual element acting as a scale that encodes numerical values, e.g. all possible normalized prediction score values that can be generated by a prediction.

A "mobile device" as used herein is a computing device small enough to hold and operate in the hand. The mobile device comprises a display, typically an LCD flat screen interface, providing a touchscreen interface with digital buttons and keyboard or physical buttons along with a physical keyboard. The mobile device can connect to the Internet and interconnect with other mobile devices and/or server computers via a network, in particular a cellular network and optionally also a WLAN-mediated internet connection. Integrated cameras, digital media players, the ability to place and receive telephone calls, video games, and Global Positioning System (GPS) capabilities can also be part of the mobile device. Power is typically provided by a lithium battery. Mobile devices may run mobile operating systems that allow third-party apps specialized for said capabilities to be installed and run. For example, the mobile device can be a mobile phone, in particular a smart phone, tablet computer or a personal digital assistant (PDA).

A "matrix display" as used herein is a display device used to display information on a device, e.g. machines, computers, telecommunication devices, clocks, railway departure indicators and many other devices. The display consists of a matrix of lights or mechanical indicators arranged in a rectangular configuration (other shapes are also possible, although not common) such that by switching on or off selected lights, text or graphics can be displayed. A matrix controller converts instructions from a processor into signals which turns on or off lights in the matrix so that the required display is produced. A matrix display can be, for example, an LCD display, in particular an LCD touch screen display.

The "rendering" as used herein is as used herein is the process of adding color, shading, and texturing of an image, in particular a vector image.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and other aspects will now be described by way of example with reference to the accompanying drawings, of which:

FIG. 3 depicts a list of prediction results respectively visualized via thumbnail icons;

FIG. 1 depicts a flowchart of a method 100 of visualizing a model based prediction and the prediction quality. The prediction result and the model quality are visualized in a dense, "compressed" manner, i.e., a large amount of information is presented on a small area such that a user can intuitively recognize the information encoded therein. The method will be described in the following by making reference also to elements of other figures, in particular FIGS. 2 and 10.

Figure 1:
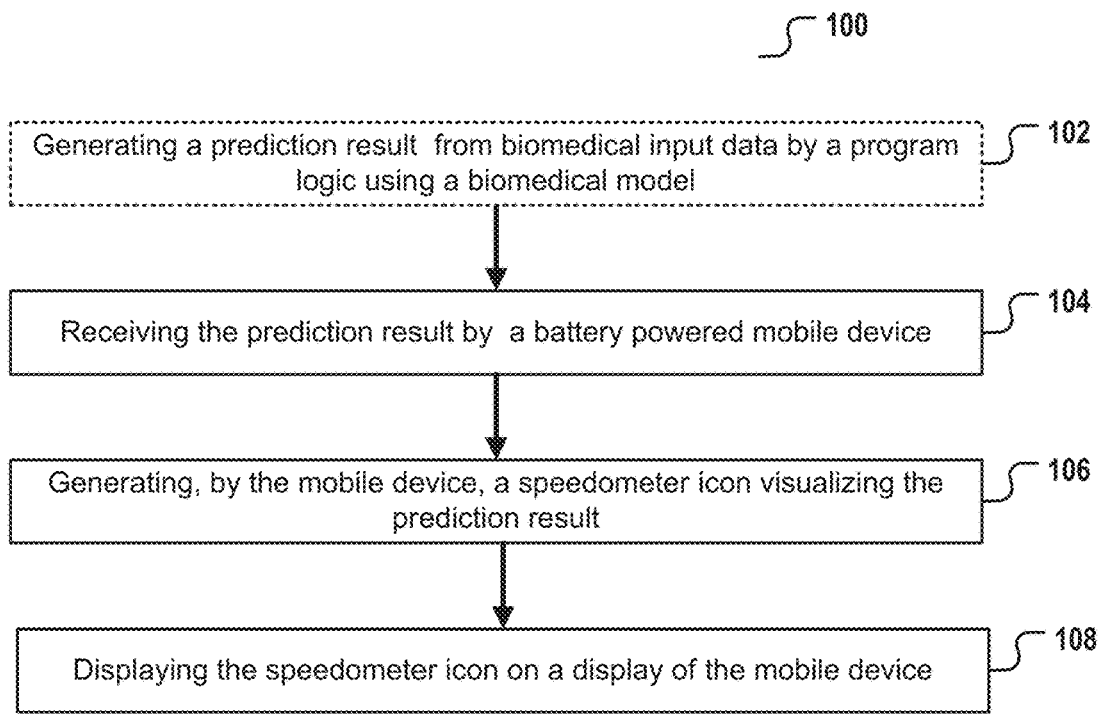
FIG. 1 depicts a flowchart of a method of visualizing a model based prediction and the prediction quality.

The method can be implemented, for example, by a client application 980 of a mobile, battery-powered device 970 that is interoperable with a backend program 962 of a server system and adapted to receive a prediction from the backend program via a digital cellular mobile telecommunication network. Alternatively, the method can be implemented in a stand-alone application instantiated on the mobile device that is adapted to extract a prediction result from a message received via the network. For example, the message can be received in the form of an e-mail or SMS or any other message format from a server computer. Still alternatively, the method can be implemented by a browser plug-in that is configured to visualize data contained in a web page or can be implemented as script code embedded in a webpage provided by a server computer to the mobile device via the network. In other embodiments, the method is implemented by a hardware logic, firmware logic, software logic or any combination thereof that is contained in the mobile device and is adapted to receive and display the prediction result and to display the analog scale icon generated therefrom.

The method 100 allows to densely visualize the result of a model-based prediction and the certainty of said prediction on a matrix display of the battery powered hand held mobile device 970. The expression "densely displaying" as used herein means that a lot of information is displayed on a very limited display space, e.g. the display of a mobile phone.

First in step 102, the mobile device 970 receives a prediction result 960. The prediction result can be received via the digital cellular mobile telecommunication network 990 from the server system 950. The prediction result has been generated for solving a particular biomedical prediction task. The prediction result has been generated by a program logic 956 using a biomedical model 958. For example, the program logic having generated the prediction can be a trained machine learning logic, e.g. a trained artificial neural network, a trained support vector machine, or any other type of program logic adapted to generate a prediction in form of a prediction score value. For example, the prediction logic can also be implemented as a manually specified set of rules and heuristics.

The biomedical model can be an explicitly specified model, e.g. a manually, semi-automatically or automatically specified model. Alternatively, the model can be an implicitly specified model that is generated during the training phase of a machine learning logic. For example, the network architecture elements of an artificial neural network that are modified in the training phase (e.g. weights of the "neurons" of the layers) in combination with the network architecture may constitute an implicit predictive model (a "black box" model) adapted for providing predictions for biomedical questions.

Figure 2A:
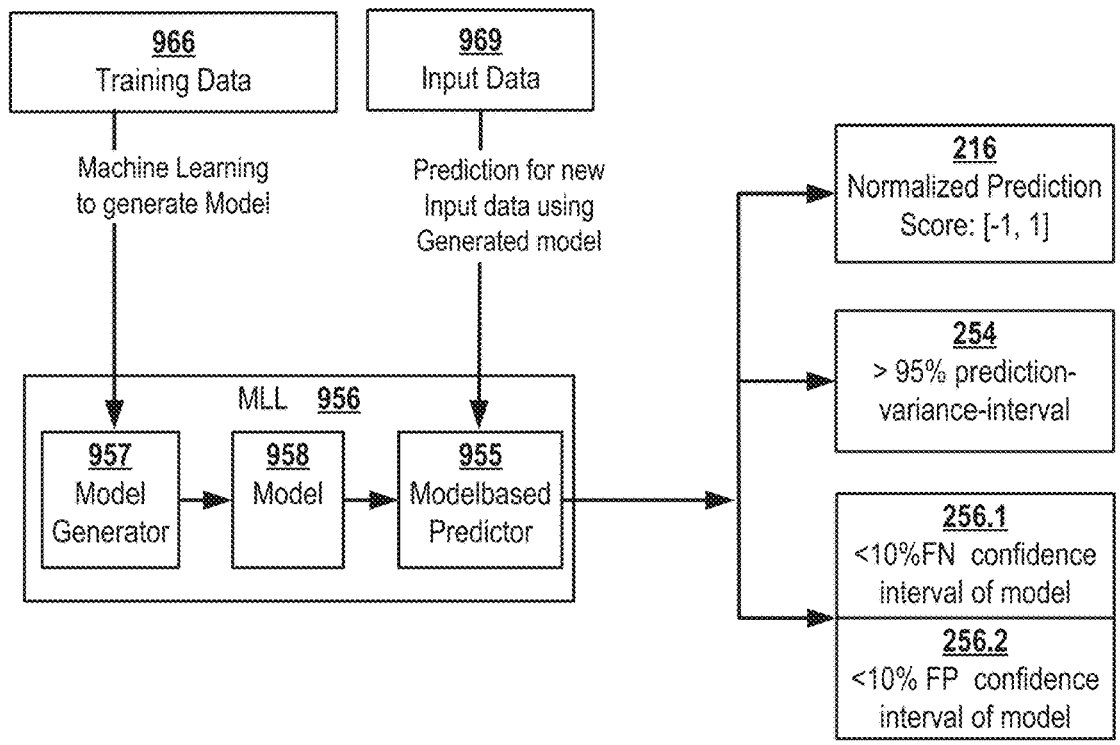
FIG. 2A depicts the generation and use of a predictive biomedical model.

As illustrated in FIG. 2A in further detail, the prediction result can comprise multiple data values. The prediction result comprises a prediction score 216, a first confidence interval 256.1 and a second confidence interval 256.2.

The prediction score is indicative of the certainty of the prediction and is a numerical value within a score range. This range can also be referred to as "interval of possible score values". For example, the score range can be a predefined range between −1 and +1 and any original score value output by the model-based prediction logic is normalized to a numerical value between −1 and +1. Depending on the type of prediction, other score ranges may be used for normalization, e.g. a range between 0 and 1. In the following examples, a score range from −1 to +1 will be used, but this range is an example only and any other predefined score ranges may likewise be used for normalizing an originally provided score value.

The first confidence interval 256.1 is a first sub-interval of the score range and is indicative of the model-specific sub-range of score values known to have a percentage of false negative (FN) predictions below a predefined FN-percentage threshold. For example, the first confidence interval 256.1 can be the sub-interval of the score ranges for which it is known, e.g. based on a statistical analysis of a plurality of model predictions, that any prediction score within this sub-interval has a likelihood of being a false negative score value that is less than the predefined FN-percentage threshold, e.g. less than 10%, or less than 5%, or less than 1%. The suitable size of the FN-percentage threshold preferably depends on the type of prediction that is computed: in case a false negative result would impose significant financial or health-related costs on a patient or the society, the predefined FN-percentage threshold is chosen such that the resulting first sub-range is comparatively narrow. For example, the first sub-range is chosen such that it covers only score values known to comprise a false negative (FN)-percentage of less than 5%. To the contrary, in case a false negative result would not impose significant financial or health-related costs on a patient or the society, the predefined FN-percentage threshold is chosen such that the resulting first sub-range is comparatively broad. For example, the first sub-range is chosen such that it covers only score values known to comprise a false negative percentage of less than 25%. In some embodiments, the first sub-range selectively covers score values known to comprise a false negative percentage of less than 10%.

The second confidence interval 256.2 is a second sub-interval of the score range and is indicative of the model-specific sub-range of score values known to have a percentage of false positive (FP) predictions below a predefined FP-percentage threshold. For example, the second confidence interval 256.2 can be the sub-interval of the score ranges for which it is known, e.g. based on a statistical analysis of a plurality of model predictions, that any prediction score within this sub-interval has a likelihood of being a false positive score value that is less than the predefined FP-percentage threshold, e.g. less than 10%, or less than 5%, or less than 1%. The suitable size of the FP-percentage threshold preferably depends on the type of prediction that is computed: in case a false positive result would impose significant financial or health-related costs on a patient or the society, the predefined FP-percentage threshold is chosen such that the resulting second sub-range is comparatively narrow. For example, the second sub-range is chosen such that it covers only score values known to comprise a false positive-percentage of less than 5%. To the contrary, in case a false positive result would not impose significant financial or health-related costs on a patient or the society, the predefined FP-percentage threshold is chosen such that the resulting second sub-range is comparatively broad. For example, the second sub-range is chosen such that it covers only score values known to comprise a FP-percentage of less than 10%.

Figure 2B:
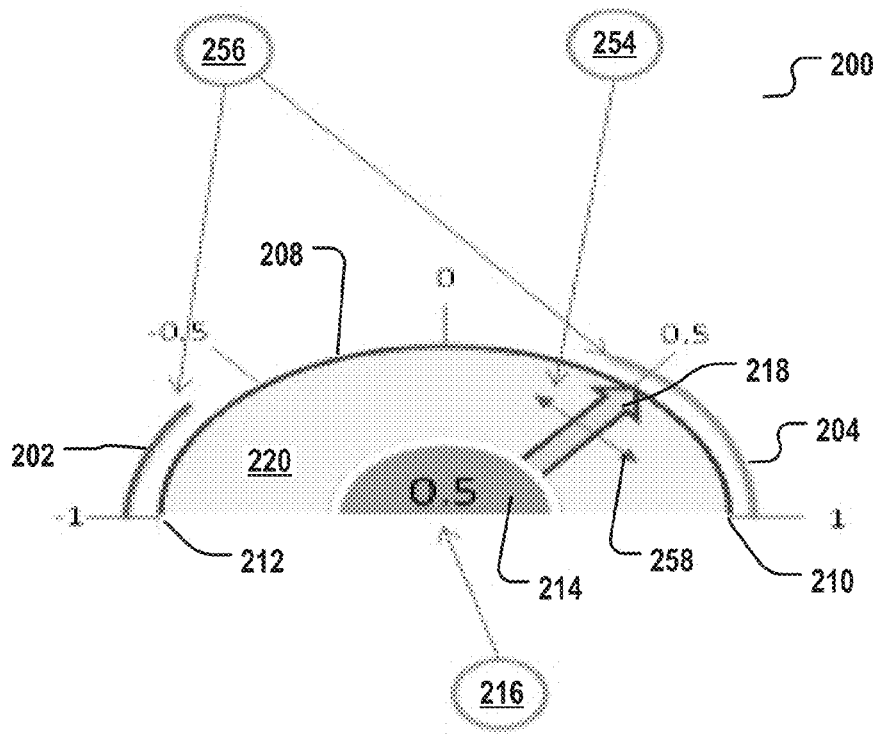
FIG. 2B depicts an analog scale icon representing a prediction result.
Figure 2C:
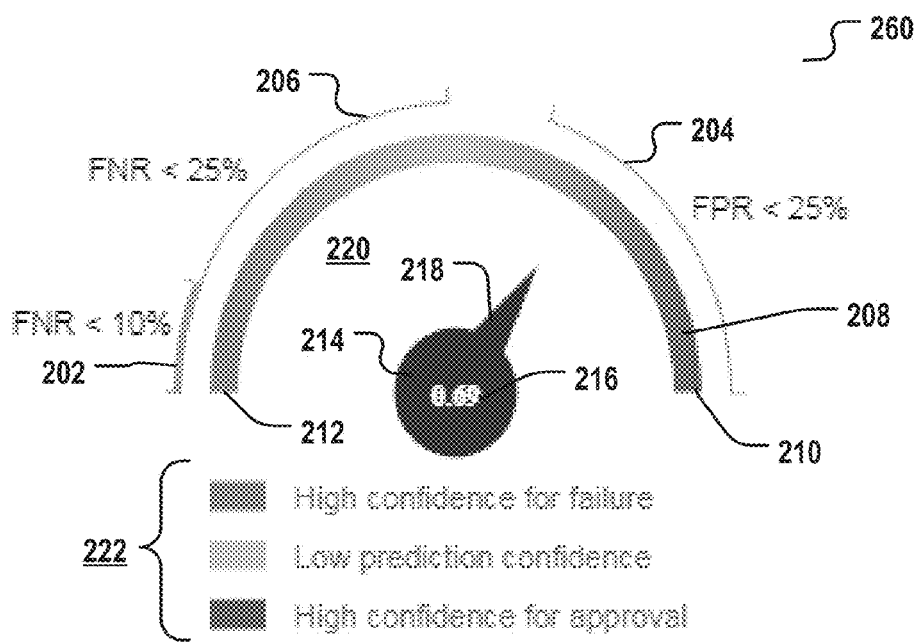
FIG. 2C depicts another analog scale icon representing another prediction result.
Figure 9:
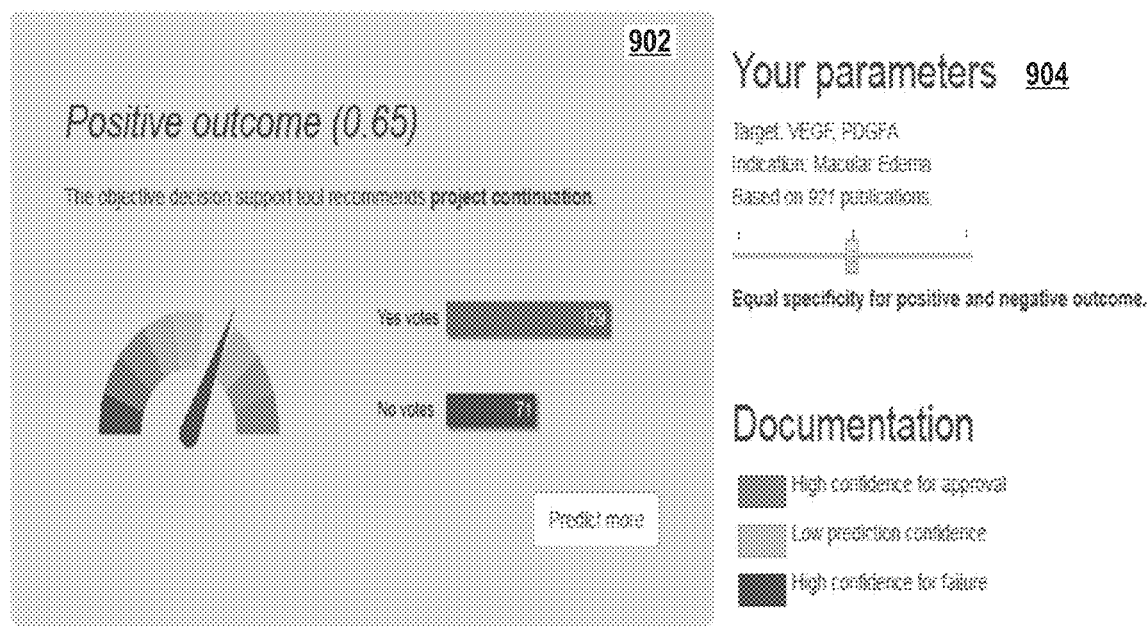
FIG. 9 depicts an analog scale icon representing an integrated prediction generated by an integrated model.

In step 106, the mobile device according to some embodiments generates an analog scale icon 200, 260 as depicted, for example, in FIGS. 2B, 2C and 9 from the prediction result. In other embodiments, this step is performed remotely, e.g. by the server computer that has provided the prediction result to the mobile device. In this case, the prediction result can be received by the mobile device in the form of numerical values and value ranges or in the form of the already generated analog scale icon that graphically indicates these values, e.g. in the form of particular sub-range indicators or text strings which are part of the analog scale icon.

In some embodiments, the analog scale icon is generated in the form of a bitmap image. In other embodiments, the analog scale icon is generated in the form of a vector image. When the analog scale image is displayed on the matrix display, the mobile device is preferably adapted to adapt the size of the analog scale icon such that is covers at least 50%, preferably at least 70%, preferably at least 90% of the display. For example, the analog scale icon can be displayed on the screen in "full screen mode".

The analog scale icon comprises a background area 220 which comprises the prediction score 216 and an analog scale 208. Preferably, the prediction score is positioned at the center of the background area.

The analog scale represents the score range. The scale has two ends 210, 212 which represent the maximum and minimum score values of the score range. For example, the scale can have the form of an arc of a semicircle or parts thereof, or can be a horizontal or vertical line or bar or can have any other shape that preferably comprises two easily recognizable ends. In some embodiments, the analog scale icon can have the design of the scale area of an analog measuring device. For example, the analog scale icon can be designed to represent a speedometer, the scale of a balance, a thermometer or the like. Thus, the scale can have e.g. the form of a bow, e.g. of a semicircle arc, or of a straight line. The scale and the background area can be designed such that they represent a virtual measurement device analog scale.

In some embodiments, the scale comprises scale values. In other embodiments, the scale is free of scale values. In some cases, the scale values may be too small for being readable by a human eye, even in case the analog scale icon is displayed on the matrix display in full screen mode. Nevertheless, a user will be able to interpret the prediction result and its quality based on the position of the pointer and the size and position of the sub-range indicators. The analog scale icon further comprises a pointer 218 pointing towards a location within the scale that represents the prediction score. For example, the background area can be a semicircle representing a speedometer. The scale can be an arc that corresponds to a part of the outline of the background area. The pointer can originate in the center of the background area.

The analog scale icon further comprises a first sub-range indicator 202 and a second sub-range indicator 204. The first sub-range indicator is a graphical element of the analog scale icon that is aligned with the scale such that the size and position of the first sub-range indicator relative to the scale is indicative of the size and position of the first confidence interval within the score range. The second sub-range indicator is a graphical element of the analog scale icon that is aligned with the scale such that the size and position of the second sub-range indicator relative to the scale is indicative of the size and position of the second confidence interval within the score range.

Next in step 108, the mobile device displays the analog scale icon on its matrix display 978. In case the analog scale icon is a vector graphic, the displaying step can comprise a rendering step for assigning colors, shades and other features dynamically to the vector-based design elements of the icon. The displaying comprises adapting the size of the analog scale icon such that it fills a predefined portion of the matrix display, e.g. at least 50% of the display, or at least 80% the display, or 100% of the display.

FIG. 2A depicts the generation and use of a predictive biomedical model according to an embodiment of the invention. For example, the model 958 can be an implicit model of an artificial neural network that was learned implicitly by the network 956 in a training phase. The machine learning logic 956 can be a prediction logic having been trained to predict, based on an analysis of biomedical literature, whether a particular drug will be accepted by the FDA as a treatment for a particular disease or not. For example, the network 956 can initially be trained on a large literature corpus such as the MEDLINE literature database used as training data 966. During the training of the machine learning logic on the training data 966, the model 958 is explicitly or implicitly learned. The functionality of learning a model 958 from training data 966 is illustrated as model generation unit 957, although the model generation process may be an implicit part of the machine learning logic 956 that has not been explicitly specified by a human programmer. The MLL can be implemented using a large variety of programming techniques and/or readily available machine learning tools, libraries and modules. In some embodiments, the logic for training the model and for applying the trained model on some new input data can be implemented in different program modules. In some other embodiments, the biological model is an integral part of the program logic that is trained and/or that performs the prediction, so it may not be possible to separate the biological model from the program logic that generates or uses it. For example, the model may be based on a neural network architecture configured to receive input data and features of a particular type and whose weights in the different network layers have been adapted during the training phase thus that the trained neural network architecture is able to perform a prediction based on new input data that corresponds to the structure and type of data used in the training phase.

Once the model 958 has been generated, the machine learning logic 956 can use the model 958 to solve a particular prediction problem. For example, a model-based prediction unit 955 can receive some input data 969, e.g. a specification of the name of one or more target molecules of the drug of interest. The prediction unit 955 can then analyze the currently available literature for identifying documents or document abstracts mentioning the names of the one or more target molecules as well as the name of the disease to be treated and analyzing meta-data associated with the identified documents. For example, the predictor can analyze the author names, publication date, cross references to other documents, the names of diseases, metabolites, genes or drugs mentioned in the documents for extracting a plurality of literature-based features for the one or more target molecules provided as input. The feature extraction can be a data analysis step that is explicitly or implicitly specified in the code of the prediction logic 956. The extracted features are then used as input for the model 958 which generates a prediction whether the drug whose targets were provided as input 969 will be approved by the FDA in the future as a treatment for a particular disease or not. The feature extraction can also be performed in the training phase for extracting features from the training data that are actually fed into the model to be trained.

The prediction result comprises a normalized prediction score 216, a first confidence interval 256.1 and a second confidence interval 256.2 indicating score value sub-ranges with a particular low ratio of false positives or false negatives results. Optionally, the prediction result further comprises a prediction-variance-interval 254.

If the prediction result is that the FDA will with 100% likelihood approve the drug, the prediction score (that may be optionally normalized) is, for example, 1. If the prediction result is that the FDA will with 100% likelihood reject approval of the drug, the prediction score (that may be optionally normalized) is, for example, −1. Typically, the prediction score will have a numerical number greater than the minimum value of the scale (greater than −1) and smaller than the maximum value of the scale (smaller than +1).

For example, a prediction score of 0.7 indicates that a particular drug whose respective target molecule name was provided as input to the prediction logic 956 is predicted to be highly likely approved by the FDA. A prediction score of −0.8 indicates that a particular drug whose respective target molecule name was provided as input to the prediction logic 956 is predicted to be highly likely rejected (not approved) by the FDA. A prediction score of about 0 indicates that the model is not able to clearly predict, for the input data 969 currently provided, whether or not the FDA will approve the drug or not, because the likelihood of refusal and the likelihood of acceptance are considered identical or highly similar by the model. A user can easily and intuitively understand the prediction result simply by having a short look on the position of the pointer: a pointer that points towards to a scale region close to the end of the scale representing the minimum scale value indicates a rejection of the hypothesis/a very low prediction score; a pointer that points towards a scale region close to the end of the scale representing the maximum scale value indicates acceptance of the hypothesis/a very high prediction score; a pointer that points towards the center region of the scale indicates that the prediction result is ambiguous and vague.

Preferably, the model generation based on the training data is performed fully automatically, e.g. within a computer implemented model generation and update framework. For example, the training data 966 can be updated and supplemented with additional data on a regular basis, e.g. once a week or once a month. This may be highly advantageous in biomedical domains where the amount of available data is rapidly increasing. This is the case for example for biomedical literature data. The model generation and update framework is preferably configured such that whenever the training data 966 is supplemented with additional training data or is modified by removing or replacing some parts of the training data, the machine learning logic 956 is automatically re-trained on the updated version of the training data 966. Thereby, also an updated version of the biomedical model 958 is automatically generated. If the updated version of the model is used for computing the same prediction on the same inputs data 969 a further time, the prediction result will differ from the previously generated prediction results, because the model has integrated additional, new knowledge that may have an impact on the outcome of a prediction.

According to some embodiments, the literature-based training and the model-based prediction is performed as described, for example, in PCT/EP2017/060844 whose disclosure is incorporated herein by reference in its entirety.

FIG. 2B depicts an analog scale icon 200 representing a prediction result. The analog scale icon in this embodiment is similar to a speedometer.

The icon comprises a background area 220 in the form of a semicircle or semi-ellipsoid. It comprises a central area 214 that also is a semicircle or semi-ellipsoid having a different color than the background area. The prediction score 216 is contained in the central area.

The scale 208 is the arc of the semi circle. A first end 212 of the scale represents the minimum possible normalized prediction score value −1, a second end 210 of the scale represents the maximum possible normalized prediction score value +1 and the center point of the scale represents the scale value "0". The scale also shows the scale values "−1", "0" and "+1". In other embodiments, no scale values, other scale values or additional scale values can be displayed.

The icon 200 further comprises a pointer 218 in the form of an arrow. The pointer originates at the center of the background area and points towards a location within the scale that represents the prediction score "0.5" that is also shown in the central region 214. Thus, even in case a user has no time to "read" the numerical value shown in area 214, and even in case the number shown in 214 is too small to be readable by a human eye, the user can nevertheless easily recognize that the prediction score is somewhere between "0" and "+1" and is therefore indicative of a "positive" prediction that the hypothesis is "true", e.g. that the FDA will "allow" a particular drug for treating a particular disease.

The icon 200 further comprises a first sub-range indicator 202 that is aligned with the scale such that the size and position of the first sub-range indicator relative to the scale is indicative of the size and position of the first confidence interval within the score range. In the depicted example, the first sub-range indicator is an arc of a (not visible) circle segment that originates at the center of the background region and that exactly covers the scale region representing the first confidence interval.

The icon 200 further comprises a second sub-range indicator 204 that is aligned with the scale such that the size and position of the second sub-range indicator relative to the scale is indicative of the size and position of the second confidence interval within the score range. In the depicted example, the second sub-range indicator is an arc of a (not visible) circle segment that originates at the center of the background region and that exactly covers the scale region representing the second confidence interval.

The first and second sub-range indicators respectively can be a segment arc, in particular a circle segment arc.

Thus, a user just has to check whether the pointer 218 points to a region of the scale that is aligned with the second sub-range indicator or not. In the depicted example, the arrow 218 points to a scale region that is aligned to the second sub-range indicator 204. This implies that the prediction score 0.5 is within the second confidence interval and has a likelihood of being a false positive prediction result that is lower than a predefined FP threshold value, e.g. below 10%. Checking whether a pointer points to a region within an arc 204 or not can be performed quickly and intuitively and without consciously comparing numerical score values with confidence intervals of the model.

The variance bar 258 is an optional element that visualizes the prediction-variance-interval, i.e., visualizes if the outcome of a prediction would be very different from the current prediction output if the input data used for the prediction would be modified slightly. If the prediction is robust against small changes of the input parameter values, the prediction variance bar is short, indicating that the prediction would not change much. If the prediction is sensitive to small changes of the input parameter values, the prediction variance bar is broad, indicating that the prediction would change significantly. In the depicted example, the scale is represented as a thick line along parts of the outline of the background area 220.

FIG. 2C depicts another analog scale icon 260 representing another prediction result. The analog scale icon in this embodiment is similar to another speedometer.

The icon comprises the visual elements having been described already for FIG. 2B. In addition, it comprises a further sub-range indicator 206 that is aligned with the scale such that the size and position of the further sub-range indicator relative to the scale is indicative of the size and position of the further confidence interval within the score range. In the depicted example, the further sub-range indicator is an arc of a (not visible) circle segment that originates at the center of the background region and that exactly covers the scale region representing a further confidence interval. For example, the first sub-range indicator 202 may indicate a score value range for which the model is known to generate a ratio of FN results that is below a threshold, e.g. below 10%. The further sub-range indicator 206 may indicate a score value range for which the model is known to generate a ratio of FN results that is below another threshold, e.g. below 25%.

In the depicted example, the scale 208 is represented as a thick bow that represents a part of the outline of the background area 220. The scale does not comprise any displayed scale values, but the sub-range indicators comprise labels being indicative of the maximum possible fraction of FP or FN predictions at the score ranges indicated by the indicators 202, 204 and 206, respectively. The icon 260 has a pointer having the shape of a needle or triangle instead of an arrow.

The optional legend 222 may provide further information assisting in the interpretation of the icon 260, e.g. a color code explanation of the colors in the color gradient comprised in the scale.

FIG. 3 depicts a list 302 of prediction results respectively visualized via thumbnail icons. The mobile telecommunication device may receive a plurality of prediction results via the network.

The plurality of prediction results can comprise two or more prediction results provided by the same model for different prediction tasks, whereby different prediction tasks are associated with the provision of different input data to the prediction logic. For example, a first task may be the prediction whether a particular drug X having the target PDCD1 will be approved by the FDA as a treatment for melanoma, and a second task may be the prediction whether same drug X having the same target PDCD1 will be approved by the FDA as a treatment for breast neoplasms. For the two different prediction tasks whose prediction results are contained in the list 302, the same literature-based biomedical prediction model can be used.

In addition, or alternatively, the plurality of prediction results can comprise two or more prediction results provided by different models for the same or for different prediction tasks. For example, a first prediction result can be generated by a literature-based model 958 ("M1") for a prediction task whether a particular drug X having the target PDCD1 will be approved by the FDA as a treatment for melanoma. A second prediction result can be generated by another model M2 for the same prediction task. The other model may not be a literature-based model, but rather a model that uses metabolic flux analysis, molecule interaction simulation logic or toxicity simulation logic for predicting whether a particular drug X having the target PDCD1 will be approved by the FDA as a treatment for melanoma. Alternatively, the other model may also be a literature-based model, but the prediction may be based on semantic analysis of the literature while model M1 may be a co-occurrence based model.

In addition, or alternatively, the plurality of prediction results can comprise two or more prediction results provided by different versions of the same models for the same or for different prediction tasks. For example, a first prediction result may indicate whether a particular drug X having the target PDCD1 will be approved by the FDA as a treatment for melanoma, whereby a particular version v1 of a literature-based biomedical prediction model was used for generating the prediction.

The model version v1 may have been trained on a literature database as of Jan. 1, 2016. A second prediction result may also indicate whether a particular drug X having the target PDCD1 will be approved by the FDA as a treatment for melanoma, whereby version v2 of the literature-based biomedical prediction model was used for generating the prediction. The model version v2 may have been trained on a literature database as of Feb. 1, 2016. A plurality of further prediction results may have been received in respect to the same prediction task, whereby each of the further prediction results corresponds to a further version of the literature-based biomedical prediction model, e.g. for Mar. 1, 2016, Apr. 1, 2016, and so on.

Each list item 304, 306 comprises at least a thumbnail analog scale icon and optionally one or more data values. The data values can comprise, for example, numerical values like the prediction score, the prediction task (project type, target, indication, etc.), and other meta-data of the prediction or the model that was used for the prediction. Each item can further comprise a link "detail" or other selectable GUI element allowing a user to select a particular list item for triggering the display of the analog scale icon in a new view that replaces the list 302. For example, the new view can comprise a full-screen version of the analog scale icon.

Thus, the use of thumbnail analog scale icons in a list of prediction results allows a user to easily compare the prediction scores and the quality of a plurality of predictions provided by different models, different model versions and/or different predictive tasks. Thus, a dense visualization of a plurality of highly heterogeneous predictive models and software programs is provided that allows a user to compare the prediction results and the prediction qualities provided by many different models. This is particularly advantageous in the context of life science research and drug development, because these technical fields are characterized by highly heterogeneous IT frameworks, a rapidly increasing amount of structured and unstructured data and a large plurality of different predictive approaches regarding the type of training and input data (literature, sequence data, expression profiles, 3-D structures, array data, image analysis), regarding the type of biomedical question (target prediction, toxicities prediction, drug identification, side effect prediction) and regarding the type of prediction algorithm used (neuronal networks, support vector machines, random forests, rules etc.).

Embodiments of the invention provide an intuitive, dense overview for a plurality of different models and also allows a user to monitor trends having an effect on the quality of a model. For example, if for a particular prediction task a plurality of prediction results are available having been generated by different versions of a model, then in some embodiments the analog scale icons generated for the prediction results are combined into a single moving image, e.g. an animated gif or a video clip wherein the elements of the icon, e.g. the arrow 218, the sub-range indicators 202, 204, 206 and/or the variance bar 258 may change their respective position and size. When a user clicks on the moving image, the elements of the analog scale icons change their size and or position. For example, in case different versions of a model correspond to continuously increasing training data set, it may happen that the growing amount of data available may allow increasing the accuracy and predictive power of a particular model. Thus, while the prediction scores of the initial predictions may be ambiguous and close to zero and the sub-range indicators 202, 204 may be very narrow, the prediction scores generated by later versions of the models may clearly indicate a positive (or negative) answer and the sub-range indicators 202, 204 may be very broad. In some cases, the model quality may also deteriorate in case the additional available data comprises information that is in contrast to a hypothesis that was hitherto supported by the outdated versions of the training data set. Thus, a user can easily recognize, by watching a moving image generated from a plurality of analog scale icons representing the prediction results of many different versions of the same model for the same prediction tasks, whether the quality of a model changed over time and if the change results in an improvement or deterioration of the prediction quality.

Figure 4:
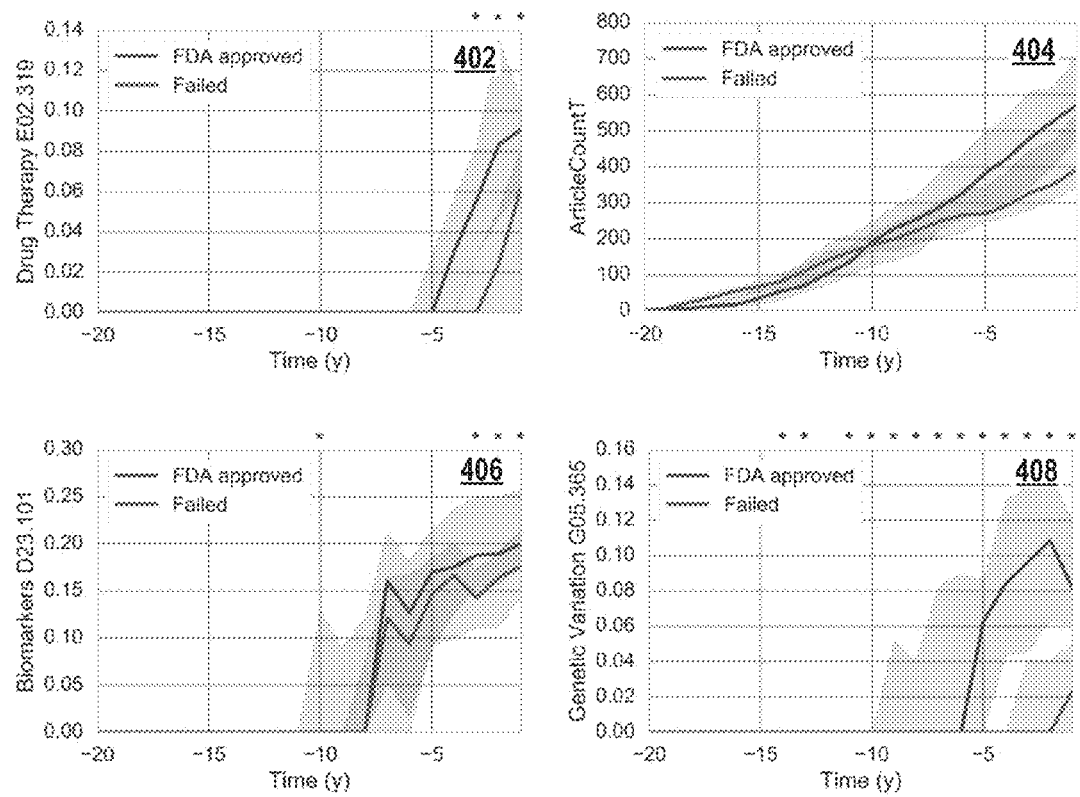
FIG. 4 depicts four plots respectively correlating FDA approval of a particular drug with the profile of a particular feature, e.g. article count.

FIG. 4 depicts four plots respectively correlating FDA approval of a particular drug with the profile of another feature, e.g. article count.

Plot 402 depicts changes in topics for publications related to successful and unsuccessful drugs over time, focusing on the topic "Drug therapy". The displayed time range are 20 years before a time point "0" which references to a specific significant time point in the development of a drug, in this case the beginning of the earliest phase 2 trial. Each publication is annotated with a limited set of topics, also called Mesh terms. Plot 402 shows the percentage of publications that are annotated with the topic "Drug therapy" for two classes of publications: the "FDA approved" publications (the upper one of the two curves at the right border of the plot) are publications that mention target and an indication of drugs that were approved by the FDA; the "Failed" publications mention the target and an indication of drugs that were terminated in phase 2 or 3. The thick lines show the median, the shaded areas the confidence interval (and implicitly the variance) of the distribution.

Statistically significant differences of the distribution as assessed by a Wilcoxon test are marked by asterisks on top of the plot. The main hypothesis proven here is that publications leading up to the development of successful drugs are annotated with the topic "Drug therapy" significantly more often before the beginning of phase 2 trials.

Plot 404 depicts a first and a second curve. The first curve "FDA approved" (the upper one of the two curves at the right border of the plot) indicates the number of articles in the Medline database mentioning the name of a particular drug target, whereby the drug was later approved by the FDA as a treatment for said disease. The second curve "failed" indicates the number of articles in the Medline database mentioning the name of a particular drug target, whereby said drug was later rejected by the FDA and was not allowed to be used for treating said disease. In the early years of an emerging research area, the two curves are very similar and it may not be possible for a literature-based model to make a clear prediction whether a particular drug will likely be approved by the FDA or not. However, after several years, it can be observed that the number of published articles mentioning a disease in combination with a drug target is higher for targets later approved by the FDA than for targets that failed. This is probably because positive results supporting a relationship between a particular drug target and a disease invite further research groups to work in this field, thereby increasing the number of publications mentioning only the target. This plot illustrates that literature-based models may reliably predict whether or not the FDA will approve a particular drug or not, in particular in later years when a sufficient number of documents is available. Thus, frequently updating literature based prediction models is key for providing high quality predictions.

Plot 406 depicts a first and a second curve. The first curve "FDA approved" (the upper one of the two curves at the right border of the plot) indicates the number of articles in the Medline database mentioning the name of a particular gene/protein being the target of a particular drug, whereby the drug was later approved by the FDA as a treatment for a disease associated with the occurrence of the biomarker. The second curve "failed" indicates the number of articles in the Medline database mentioning the name of a particular gene/protein being the target of a particular drug, whereby said drug was later rejected by the FDA and was not allowed to be used for treating a disease associated with the occurrence of said gene/protein.

Plot 408 depicts a first and a second curve. The first curve "FDA approved" (the upper one of the two curves at the right border of the plot) indicates the number of articles in the Medline database mentioning the topic genetic variation and the name of a particular drug target and its indication, whereby the drug was later approved by the FDA. The second curve "failed" indicates the number of articles in the Medline database mentioning the topic genetic variation and the name of a drug target and its indication, whereby said drug was later rejected by the FDA. Thus, information on how many publications mention the topic genetic variation may be used as training data for generating a further predictive model adapted to predict, based on genetic variation data, whether or not a particular drug will be approved by the FDA or not.

Figure 5:
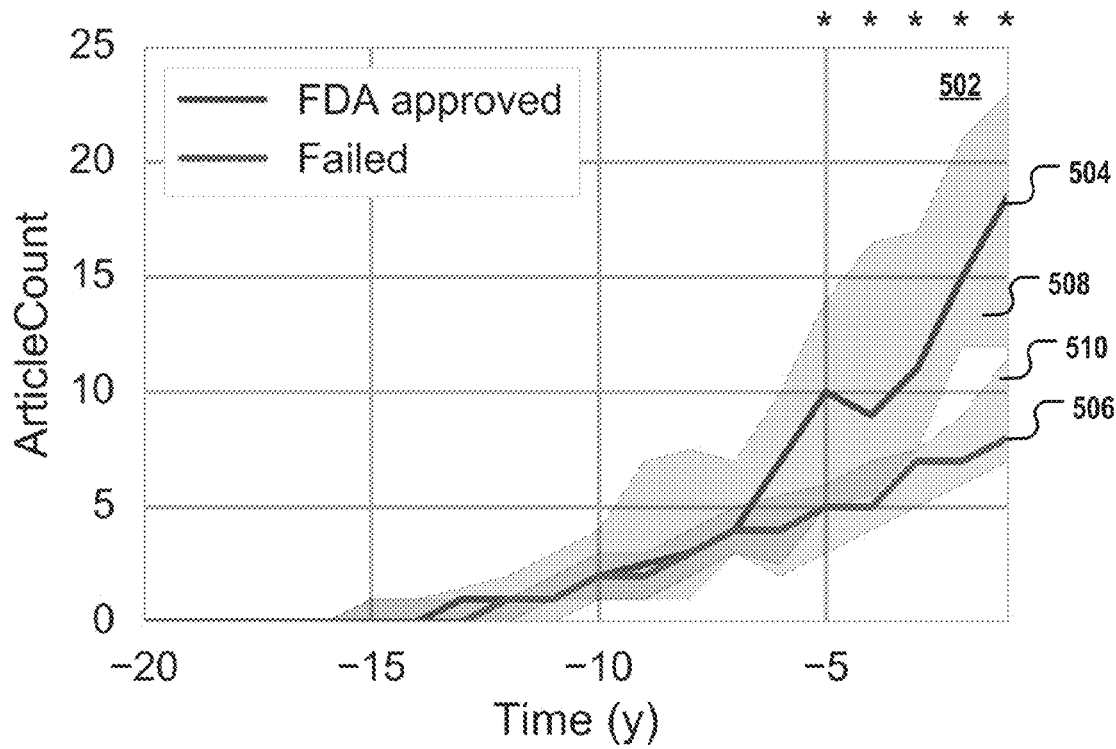
FIG. 5 depicts a plots correlating FDA approval of a particular drug with article count.

FIG. 5 depicts a plot 502 correlating FDA approval of a particular drug with article count. The time when the earliest phase 2 trial of particular drug starts is the time "0" and the plot 502 thus shows the article counts 20 years ahead of this beginning of phase 2 and even further ahead of the final decision of the FDA upon approval or rejection of the drug. It can be seen that the article count is very similar in the time 20 years ahead of the decision time till about 7 years ahead of the entry into phase 2. Then, the publication count of documents mentioning a disease in combination with a particular drug target is significantly higher for drug targets of drugs that will later be approved by the FDA. Five years before entry into phase 2 of the drug the difference is statistically significant, as indicated by the asterisks on top of the plot. Thus, literature based models that use article count together with other discriminatory features such as those shown in FIG. 4 may be able to predict at the entry into phase 2 trials, years ahead of the actual decision of the FDA, if a particular drug should still be considered as a promising candidate for FDA approval and if further money and effort should be invested in pre-clinical and clinical research related to this drug.

This is an important finding, because a scientist may manage a large amount of pre-clinical trials and may be interested in even more hypothetical drug-disease combinations that may be of interest for future research work. By automatically generating literature-based predictions for a plurality of prediction tasks related e.g. to a plurality of different diseases, drugs, drug candidates and combinations thereof, and by repeatedly and fully automatically updating the literature-based models and the predictions generated based on said models, an automated prediction and alert system may be provided allowing this scientists or a plurality of scientists having registered for a plurality of different prediction tasks to keep-up to date and stop expensive research when the chances of success are low.

Figure 6:
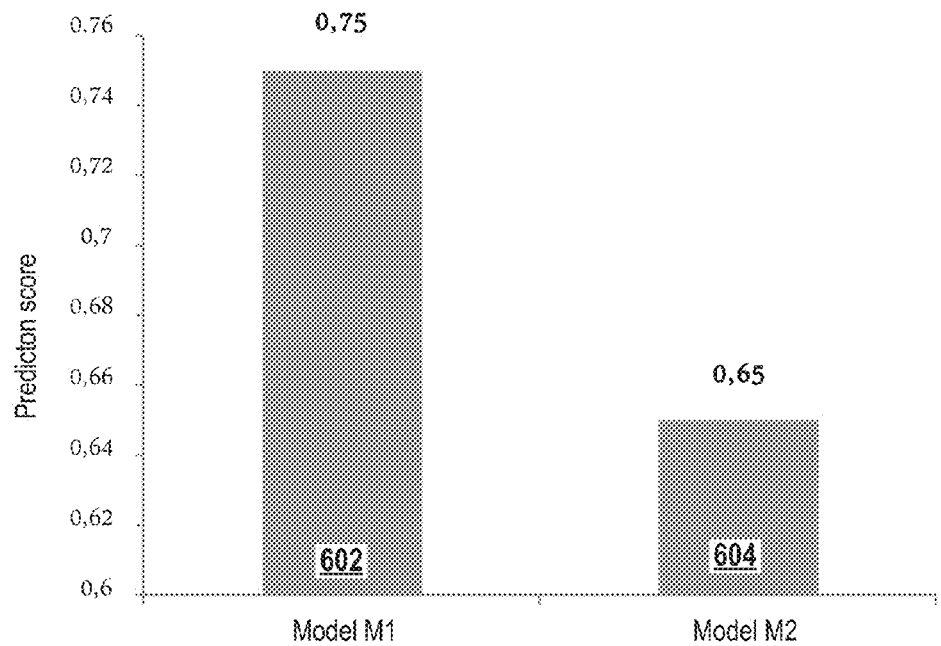
FIG. 6 depicts two prediction scores generated by different models for the same predictive task.
Figure 7:
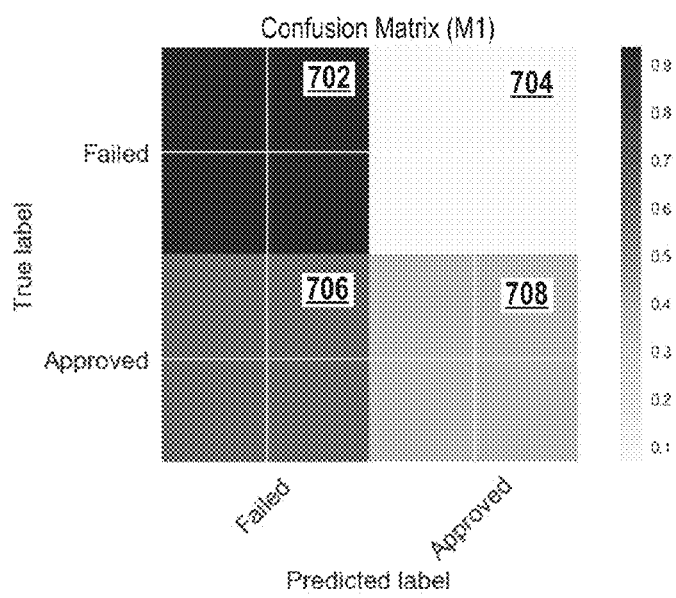
FIG. 7 depicts a confusion matrix associated with a particular model.
Figure 8:
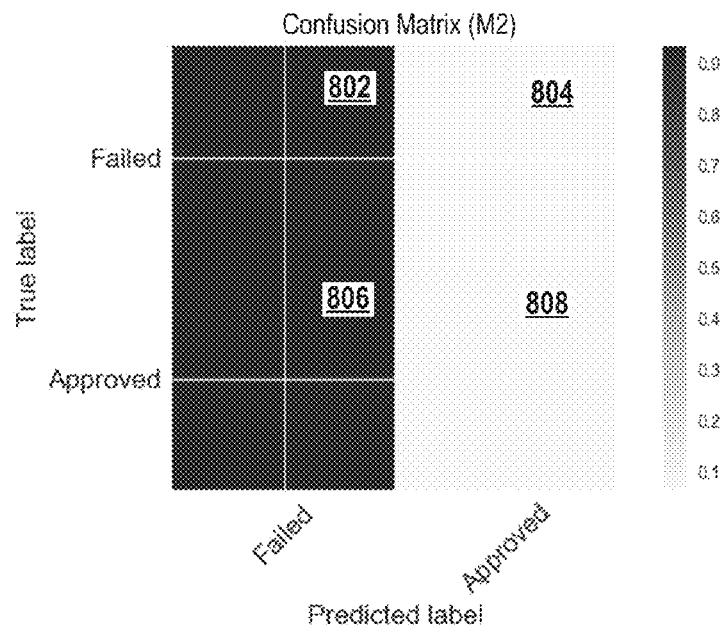
FIG. 8 depicts a confusion matrix associated with another model.

FIG. 6 depicts two prediction scores generated by different literature based models M1, M2 for the same predictive task. For example, a first model based prediction logic MLL1 having been trained on biomedical literature may generate a prediction result for the question if a particular drug X will be approved by the FDA for treating a disease D with a prediction score of 0.75. A second model based prediction logic MLL2 having been trained on the same biomedical literature using a neural network for the same question may generate a prediction result with a prediction score of 0.65. Thus, a user may be faced with the problem of deciding which one of the predictions should be trusted. In order to assess the quality of a prediction model confusion matrices as depicted in FIGS. 7 and 8 are commonly used for determining which one of the models M1, M2 and/or respective prediction logics MLL should be considered as more accurate and trustworthy. For example, the models M1, M2 can be neural networks or random forest models.

FIG. 7 depicts a confusion matrix associated with a particular model M1, e.g. the model M1 whose prediction result is depicted in FIG. 7 having output the prediction score 0.75.

FIG. 8 depicts a confusion matrix associated with the model M2 having output the prediction score 0.65. The confusion matrices comprise color-coded frequencies for true negative predictions 702, 802, false positive predictions 704, 804, false negative predictions 706, 806, and true positive predictions 708, 808. However, a user has to inspect a plot with the prediction results as shown in FIG. 6 in combination with the two confusion matrices as depicted in FIGS. 7 and 8 in order to assess whether the prediction results of the two models and also their respective quality are similar or not. However, it is not possible to display the plots depicted in FIGS. 6, 7 and 8 on a small display of a mobile hand-held device in sufficient size as to allow a user to quickly obtain and comprehend the information comprised therein. Moreover, the scrolling movement of the user typically consumes a large amount of energy. This may discharge the battery and is therefore highly undesirable. To the contrary, embodiments of the invention provide a dense visualization of the prediction result and the quality of two or more different models, thereby easing the comparison of two or more models used for performing the same predictive task.

FIG. 9 depicts a further example of an analog scale icon displayed on a GUI 902. The icon depicted in this figure represents an integrated prediction generated by an integrated model. The integrated model uses the output generated by many different predictive models as input for generating an overall prediction result that may also comprise the elements 216, 254, 256 described already with reference to FIG. 2A. The GUI may comprise additional meta data, e.g. the predictive task, the number of publications identified mentioning the disease and the drug target, the specificity for positive and negative outcome and the like.

Figure 10:
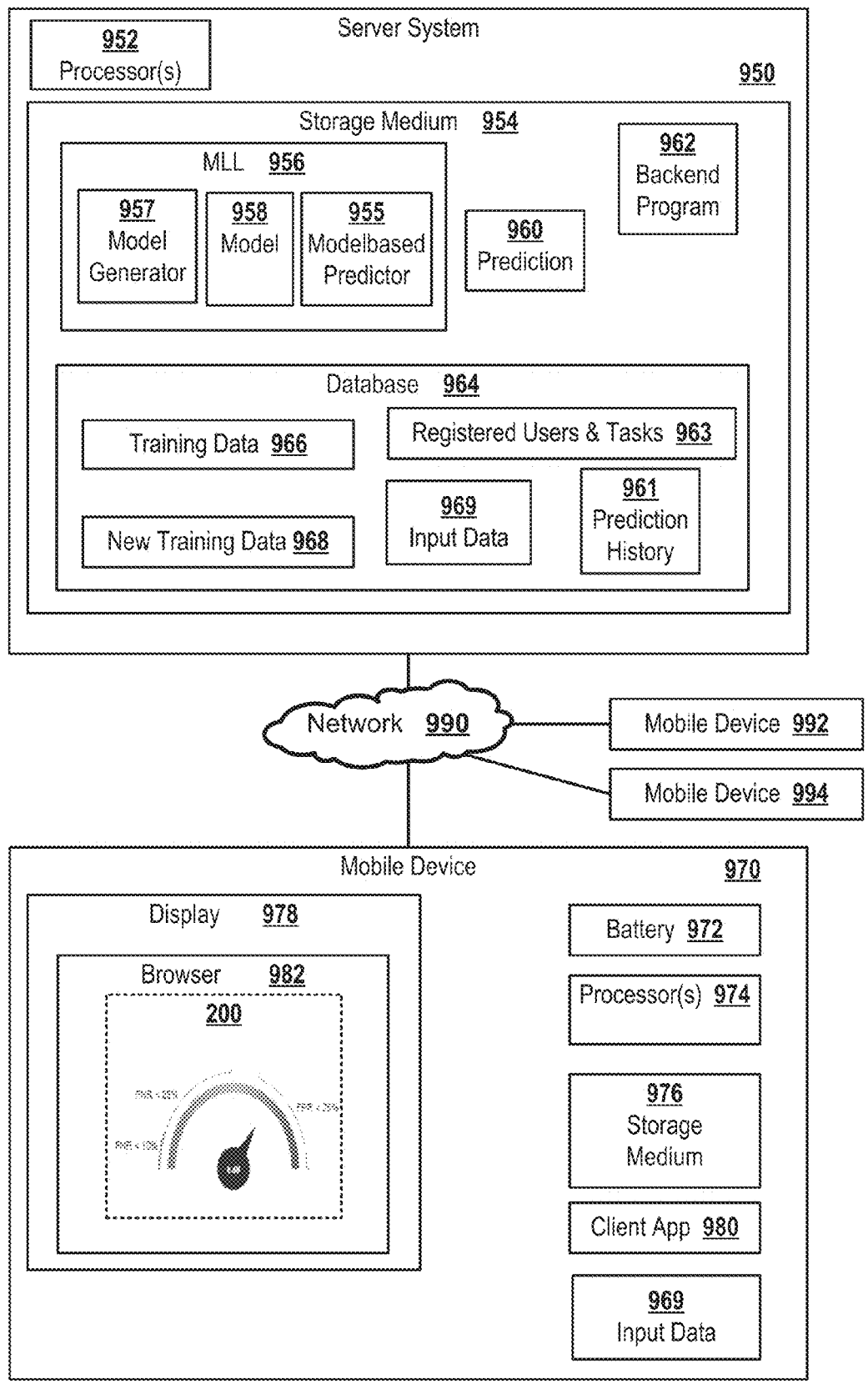
FIG. 10 depicts a block diagram of a system comprising a server computer and at least one mobile device.

FIG. 10 depicts a block diagram of a system comprising a server computer 950 and a plurality of mobile devices 970, 992, 994 which are connected to each other via a network 990. The network can be in particular a digital cellular mobile telecommunication network.

The server system 950 comprises one or more processors 952 and a non-volatile storage medium 954 comprising a model-based prediction logic 956 and a database 964. The server system can be a monolithic system or can be a distributed computer system, e.g. a cloud computer system. Likewise, the storage medium 954 can be a single physical device or can be a set of interconnected distributed storage devices.

The model-based prediction logic 956 can be a machine learning logic, e.g. a neural network, a support vector machine or the like. Functionally, the model-based prediction logic comprises a model generation functionality 957 that analyzes a set of training data 966 that is typically annotated was true positive and true negative results and thereby generates a model 958 in a so called "training phase". The model-based prediction logic further comprises a prediction functionality 955 that uses the generated model 958 to generate a prediction for a particular input data 969 that corresponds to a particular prediction task. The model generation and model-based prediction functionalities may be implemented as separate modules or even as separate application programs which are integrated into a model-based prediction framework. Alternatively, the model generation and model-based prediction functionalities can be integral part of a single piece of software. The model-based prediction logic 956 can be implemented in any programming language such as, for example, Java, C #, Perl, C++ or the like.

According to some embodiments, the server system comprises a backend program 962 configured to coordinate the exchange of request and response messages between the server and each of the mobile devices 970, 992, 994. For example, the backend program can be configured to receive a request from a mobile device 970 for performing a predictive task, e.g. for predicting, based on a literature-based model 958, whether the FDA will likely approve to using drug X is a treatment for disease D. For example, the backend program 9620 can be interoperable with a client application 980 running on the mobile device or can be interoperable with a specially designed plug-in of a browser 982 of the mobile device, whereby the plug in acts as a kind of client application. The input data 969 to be used for performing the requested prediction, e.g. the specification of the names of one or more drug targets of the respective drug X, the name of the disease D of interest and optional further parameters like the version of the model to be used for the prediction can be entered by a user via the mobile device 970 or can already be available to the backend program 962 at the moment of receiving the request from the mobile device 970. For example, the server system can comprise a database 964 comprising a list of registered users and prediction tasks 963, whereby each registered user has assigned one or more prediction tasks and whereby the input data 969 that is to be used when performing a particular prediction task for a user can already be stored in the database 964 in association with the respective prediction tasks and users.

The backend program 962 can receive a request for performing a prediction task for a particular user via the network 990 from the mobile device 9700 can receive any other trigger for initiating the performing of the prediction task. In response to receiving the request or the other trigger, the backend program forwards the input data associated with the prediction task to the model-based prediction logic 956 and triggers the model-based prediction logic to generate a prediction result 960 for the prediction task. For example, the prediction result can comprise a normalized prediction score 216, a first and a second confidence interval 25.1, 256.2 and optionally also a prediction-variance-interval 254 as described, for example, in the description of FIG. 2A and in other sections of the description. The backend program 962 forwards the prediction result 960 to the one of the mobile devices 992, 994, 970 from which the request to perform the prediction was received or to the one of the mobile devices that is assigned to the user to whom the prediction task is assigned in the user-and task-registry 963 of the database 964. In addition, the prediction result can be stored in a prediction history 961 in the database 964. Preferentially, each prediction result stored in the history 961 has assigned some meta-data, e.g. a prediction task for which the prediction was performed, one or more users having assigned the prediction task, the date of the prediction, and ID, type and/or version of the model used for the prediction, and the like. The history allows obtaining profiles of the development of the prediction score and the model-based prediction quality and certainty over the time provided that a particular prediction is repeated multiple times on updated versions of the same model for the same predictive task. These profiles can be used for generating moving images from a plurality of analog scale icons which visualize the prediction result obtained in the repeated predictions. For example, the moving images can be animated gifs or short video clips or have any other suitable data format that allows the server-side or client-side generation of a "movie-like" graphic user interface element.

The backend program 962 can return the prediction result 960 to the mobile device 970 via the network 990 via many different ways and protocols. For example, the backend program can send the prediction result 960 directly to a client application 980 using e.g. the EJB JavaBeans framework, or a web service protocol, e.g. the SOAP protocol. Alternatively, the second program 962 can send the prediction result in the form of an email, an SMS message or any other message format to the client application 986 or to any other application running on the mobile device that can be accessed and analyzed and used for extracting the message by the client application 980 or a browser plug-in acting as a client application. Still alternatively, the backend program 962 can be a web server application program that is configured to generate webpages, e.g. HTML pages, which comprises the prediction result 960. The webpage can comprise the prediction result in the form of text, e.g. HTML text elements, and/or in the form of an analog scale icon 200, 260 generated on the server side by the backend program 962. In case the analog scale icon is generated by the server, the receiving mobile device merely has to adapt the size of the icon contained in the web page such that the page in the icon contained therein fit to the dimensions of the matrix display 978 of the mobile device. In case the analog scale icon is provided in the form of a vector graphics, the displaying of the icon by the mobile device comprises rendering the vector graphic icon. Alternatively, in case the prediction result is returned in the form of numerical values and value ranges, the client application 980 is configured to generate an analog scale icon 200, 260 from the prediction result as described herein for various embodiments of the invention. The client-side generation of the icon can also be implemented by a browser plug-in acting as a client application or by a script, e.g. a PHP code or JavaScript code, Flash program code or the like, that is part of a webpage provided by a web server software used as the backend program 962.

In the example depicted in FIG. 10, the mobile device 970 is powered by a battery 972 and comprises one or more processors 974 and a non-volatile storage medium 976 where a browser 982 and a client application 980 are stored and installed.

In one embodiment, the client application is a browser-plug-in that is interoperable with the backend program 962. The client application receives the prediction result 960 in the form of numerical values and value ranges and generates an analog scale icon 200, 260 from said numerical values and value ranges. The client application 980 further creates a webpage, integrates the generated icon into the webpage and triggers the displaying of the webpage with the icon by a browser 982 on the matrix display 978.

In another embodiment, the client application is a stand-alone application that is interoperable with the backend program 962. The client application receives the prediction result 960 in the form of numerical values and value ranges and generates an analog scale icon 200, 260 from said numerical values and value ranges. The client application generates a graphic user interface (GUI) comprising the icon and displays the GUI with the icon on the matrix display. For example, the GUI can be generated using the Java swing or awt library. Alternatively, the GUI can be an HTML page and the client application 980 can act as a kind of "browser" adapted to display the HTML-based GUI.

In still another embodiment, the mobile device does not comprise any client application or clock in or at least does not require them for receiving and visualizing the prediction result 960. For example, the backend program 962 may generate a webpage comprising the prediction result 960 in the form of numerical values and value ranges and comprising a script, e.g. a JavaScript section, which is adapted to generate, when executed by a processor 974 of a client device 970, to graphically represent the individual elements of the prediction result 960 in the form of respective elements of an analog scale icon 200, 260.

Instead of a single prediction result, the mobile device 970 can also request a plurality of prediction results for one or more predictive tasks and receive a list of prediction results instead of a single result. For example, the list of prediction results can be displayed in the form of a list as depicted in FIG. 3.

The backend program 962 and/or the client application 980 can also be implemented in any programming language such as, for example, Java, C #, Perl, C++ or the like.

The above described way of requesting a prediction by the mobile device and receiving a prediction result from the server in response to the request may not be the only way of how a user may request and visualize a particular prediction. In preferred embodiments, each user having assigned one of the mobile devices 992, 994, 970 can in addition, or alternatively, receive a prediction result automatically and without an explicit request in response to the server system having generated a new version of the model 958, having repeated one or more prediction tasks associated with the user of the mobile device in the user and tasks registry 963, and having determined that at least one of the prediction results obtained using the new, updated model version is significantly different from the previously obtained prediction results for the same prediction tasks. Thereby, "is significantly different" may mean that the prediction scores are significantly different and/or that any of the confidence interval (e.g. the first confidence interval 256.1, the second confidence interval 256.2, and/or the prediction-variance-interval 254) are significantly different from the respective intervals obtained in the previous prediction for the same prediction task. In preferred embodiments, the neck and program 962 enables a user to configure, for the prediction score and/or for each of the confidence intervals 254, 256.1, 256.2 individually, a threshold that specifies what is considered by the user as "significantly different". The use of performing this configuration can be one of the user's having assigned one of the mobile devices 992, 994, 970 or can be an operator of the server system 950. For example, the user may specify that a current prediction score is significantly different from a previously obtained prediction score if the normalized score values differ from each other by more than 15%.

In addition, or alternatively, the user may specify that a first confidence interval 256.1 of a current prediction is significantly different from a first confidence interval obtained for the previous prediction for the same prediction task if the intersection interval of the two first confidence intervals is more than 15% smaller than the first confidence interval obtained for the previous prediction and/or if the size of the first confidence interval obtained for the new prediction is at least 15% larger than the size of the first confidence obtained for the previous prediction.

In addition, or alternatively, the user may specify that a second confidence interval 256.2 of a current prediction is significantly different from a second confidence interval obtained for the previous prediction for the same prediction task if the intersection interval of the two second confidence intervals is more than 15% smaller than the second confidence interval obtained for the previous prediction and/or if the size of the second confidence interval obtained for the new prediction is at least 15% larger than the size of the second confidence obtained for the previous prediction.

In addition, or alternatively, the user may specify that a prediction-variance-interval 254 of a current prediction is significantly different from a prediction- variance-interval 254 obtained for the previous prediction for the same prediction task if the intersection interval of the two prediction- variance -intervals is more than 15% smaller than the prediction- variance -interval obtained for the previous prediction and/or if the size of the prediction- variance-interval 254 obtained for the new prediction is at least 15% larger than the size of the prediction- variance-interval 254 obtained for the previous prediction.

The user can set different values for the first and second confidence intervals, the prediction- variance-interval and the score value difference threshold.

According to preferred embodiments, the program logic 962 is configured to automatically re-train the machine learning based prediction logic 956 on a regular basis and/or whenever new or additional training data 968 are available. The re-training of the machine learning logic 956 implies that a new version of the model 956 is generated that may generate different prediction results for the same prediction task than the previous model(s). The backend program 962 can be configured to automatically trigger the re-computation of prediction results based on the new model version for all prediction tasks contained in the user and task registry 961 or at least for the prediction tasks flagged with an "automated update" tag. Then, the backend program 962 compares the prediction results obtained using the new model with the respective prediction results having been obtained using the previous version of the model which have been stored in the prediction history 961. In case a particular prediction result is "significantly different" from a prediction result obtained for the same prediction task using a previous model version, all users having assigned said particular prediction task are automatically notified via an alert message by the backend program 962 that a newer prediction result is available for a prediction task assigned to said user. For example, the second program 602 may be configured to send an alert message, e.g. an email, a SMS or any other message form, to the mobile device of a user having registered for a prediction task whose prediction result is significantly affected by the model update. In some embodiments, the alert comprises a selectable element, e.g. a URL, which allows a user selecting the element to trigger the receiving of the updated prediction result and/or the receiving of an analog scale icon representing the updated prediction result. In case a user has registered for multiple prediction tasks and in case the prediction result of multiple prediction tasks have been determined by the backend program to be significantly affected (changed, modified) by the model update, the backend program can send an alert message comprising a list of updated prediction results and/or a list of analog scale icons representing the updated prediction results. Alternatively, the alarm message may comprise only a notification that a new version of a prediction model is available and that a plurality of prediction tasks are affected by the new model and a selectable element, e.g. an URL, whereby the selection of the URL by the user triggers the receiving of the list of updated prediction results and/or the receiving of a list of analog scale icons representing the updated prediction results.

This may be highly advantageous, because a user having registered for a large number of prediction tasks is not "flooded" with a large number of messages whenever a model is updated. Often, a model update will not significantly affect the outcome of a prediction and a notification of the user would just increase network traffic and disturb the user. However, in case a model update is observed to have a significant impact on a prediction result, any user having registered for the respective prediction task is automatically provided with the new, updated version of the prediction result or at least with a link allowing the user to retrieve the updated version of the prediction result., Thus, the user is relieved of the burden to repeatedly perform a particular prediction in order to make sure that the prediction results are always based on the latest available data and model version.

According to embodiments, the client applications 980, in combination with the backend program 962 and the machine learning logic 956 are part of an automated IT framework configured to automatically and repeatedly retrieve a current set of training data, re-train the machine learning logic 956 on the latest available training data for generating updated versions of predictive biomedical model(s), repeat all the predictions specified in prediction tasks in a user and task library 963 on the updated model(s) for obtaining current prediction results, comparing the current prediction results with previously obtained prediction results having been generated based on previous versions of the model(s), and selectively notifying only those registered users on a relevant model update and new relevant prediction results which have assigned in the registry 963 a prediction task whose prediction result was observed in the comparison operation to be significantly different from the prediction result obtained based on the previous model version. Thus, network traffic is avoided and a highly user-friendly system is provided that ensures that scientists and scientific managers always decide on the basis on the predictions of up-to-date models. The use of analog scale icons and respective thumbnail icons ensures that a user can quickly and intuitively assess and compare the prediction results as well as the quality of the prediction results and the quality of the underlying models and model versions also on small screens of mobile devices without performing any scrolling movement and even without having to read numerical values or value ranges.

LIST OF REFERENCE NUMERALS

100 method
102-108 steps
200 analog scale icon
202 first sub- range indicator
204 second sub- range indicator
210 and of scale representing maximum value of the prediction score range
212 end of scale representing minimum value of the prediction score range
214 center area of background area
216 normalized prediction score
218 pointer
220 background area (speedometer disk)
222 legend
254 prediction-variance-interval
258 variance bar
256.1 first confidence interval
256.2 second confidence interval
260 analog scale icon
302 prediction list
304 list item comprising a thumbnail-analog scale icon
306 list item comprising a thumbnail-analog scale icon
402-408 plots respectively correlating FDA approval of a drug with a profile of another feature
502 plot correlating FDA approval of a drug with article count
504 counted number of articles mentioning a particular drug that was later approved by FDA
506 counted number of articles mentioning a particular drug that was later rejected by FDA
508 prediction-variance-interval of the median article count for publications mentioning drug targets and indications of FDA approved drugs 510 prediction-variance-interval of the median article count for publications mentioning drug targets and indications of drugs that did not reach FDA approval
602 bar plot visualization of a prediction score generated by a random forest model
604 bar plot visualization of a prediction score generated by a base line model
702 true negative predictions
704 false positive predictions
706 false negative predictions
708 true positive predictions
802 true negative predictions
804 five positive predictions
806 false negative predictions
808 true positive predictions
902 graphic user interface comprising an analog scale icon
904 legend and meta-data of prediction
950 server system
952 processor
954 storage medium
955 model-based prediction logic
956 machine learning logic
957 model generation logic
958 predictive model
960 prediction result
961 prediction history
962 backend program
963 registered users and prediction tasks
964 database
966 training data
968 new training data
969 input data
970 mobile device
972 battery
974 processor
976 storage medium
978 matrix display
980 client application
982 browser
990 network
992 mobile device
994 mobile device

The invention claimed is:

1. A method of visualizing the certainty of a biomedical model-based prediction on a matrix display of a battery powered hand held mobile telecommunication device, the method comprising:
receiving, by the mobile device, a prediction result via a digital cellular mobile telecommunication network, the prediction result having been generated for a biomedical prediction task by a program logic using a biomedical model, the prediction result comprising at least:
a prediction score, the prediction score being indicative of the certainty of the prediction and being a numerical value within a score range, the score range being a predefined range of possible score values;
a first confidence interval, the first confidence interval being a first sub-interval of the score range, wherein the first confidence interval is indicative of the model-specific sub-range of score values known to have a percentage of false negative predictions below a predefined FN-percentage threshold;
a second confidence interval, the second confidence interval being a second sub-interval of the score range, wherein the second confidence interval is indicative of the model-specific sub-range of score values known to have a percentage of false positive predictions below a predefined FP-percentage threshold;

displaying, by the mobile device, an analog scale icon on the matrix display of the mobile device, the analog scale icon comprising:
- a background area comprising the prediction score;
- an analog scale representing the score range, wherein the ends of the scale represent the maximum and minimum score values of the score range;
- a pointer pointing towards a location within the scale that represents the prediction score;
- a first sub-range indicator being aligned with the scale such that the size and position of the first sub-range indicator relative to the scale is indicative of the size and position of the first confidence interval within the score range; and
- a second sub-range indicator being aligned with the scale such that the size and position of the second sub-range indicator relative to the scale is indicative of the size and position of the second confidence interval within the score range, the prediction result further comprising a prediction-variance-interval, the prediction-variance-interval being indicative of a sub-range of the score range, the width of the prediction-variance-interval quantifying the amount of variation or dispersion of the prediction scores computed by program logic using the biological model, and the analog scale icon further comprising a variance bar arranged perpendicular to the pointer, the width of the variance bar correlating with and being indicative of the width of the prediction-variance-interval.

2. The method of claim 1, wherein:
the analog scale icon is a speedometer icon; and/or
the background area is a tacho disc area; and/or
the scale is a part of the outline of the background area; and/or
the pointer originates at the center of the background area; and/or
the background area is a semicircle; and/or
the first and second sub-range indicators respectively is a segment arc, in particular a circle segment arc; and/or
the prediction score is displayed at the center of the background area; and/or
the analog scale icon further comprises a center area concentrically aligned with the background area, the center area displaying the score value.

3. The method of claim 1, wherein the width of the variance bar is identical to the chord length of a visible or non-visible circle segment, said circle segment originating at the center of the background area, the two ends of the variance bar intersecting with the legs of the circle segment, the arc of the circle segment being a part of the scale that corresponds to the prediction-variance-interval.

4. The method of claim 1, further comprising:
automatically generating, by the program logic using the biomedical model, the prediction result.

5. The method of claim 1, the program logic being installed on a server computer system, the method further comprising:
automatically generating, by the program logic using the biomedical model, the prediction result;
sending the prediction logic to the mobile device via a network; or
sending a message to the mobile device via a network, the message notifying the mobile device that the prediction result was generated, and downloading the prediction result by the mobile device from the server computer.

6. The method of claim 1, the program logic being a trained machine-learning logic.

7. The method of claim 6, the method further comprising:
repeatedly receiving training data, each received training data comprising at least some data not being contained in the previously received training data;
upon each receipt of training data, automatically re-training the machine learning logic on the currently received training data, thereby automatically generating an updated version of the biomedical model.

8. The method of claim 7, the biomedical model used by the machine learning logic being a first biomedical model having been generated based on first training data, the mobile device being one of a plurality of mobile devices assigned to a respective user, the method further comprising:
registering the plurality of users and a plurality of biomedical prediction tasks at a backend program, each user having assigned one or more of the prediction tasks;
performing, by the machine learning logic, each of the prediction tasks, thereby respectively using the first biomedical model for generating a first prediction result;
sending the first prediction results selectively to the mobile devices of the users to which the prediction tasks for which the first prediction results were generated are assigned;
in response to each re-training of the machine learning logic, automatically performing, by the machine learning logic, each of the prediction tasks a further time, thereby respectively using the updated version of the biomedical model for generating a second prediction result; and
sending the second prediction results or a notification of their computation selectively to the mobile devices of the users to which the prediction tasks for which the first prediction results were generated are assigned.

9. The method of claim 8, further comprising:
comparing, by the backend program, the first prediction result and the second prediction result computed for each prediction task;
performing the sending of the second prediction results or the notification of their computation selectively for those prediction tasks for which a first prediction result and a second prediction result were computed wherein:
the score value of the first prediction result but not the score value of the second prediction result lies within the first confidence interval; or
the score value of the second prediction result but not the score value of the first prediction result lies within the first confidence interval; or
the score value of the first prediction result but not the score value of the second prediction result lies within the second confidence interval; or
the score value of the second prediction result but not the score value of the first prediction result lies within the second confidence interval; or
the score value of the first and second prediction result differ by more than a predefined score difference threshold; or
the size of the prediction-variance-interval of the first and second prediction result differ by more than a predefined interval length difference threshold.

10. The method of claim 6, the machine learning logic having been trained on biomedical literature, the machine learning logic being adapted to predict the likelihood of failure of a pre-clinical or clinical trial examining the treatability of a particular disease by a particular drug using features automatically extracted from the biomedical literature.

11. The method of claim 1, further comprising:
receiving, by the mobile device, a plurality of prediction results comprising the prediction result, each of the received prediction results having been generated by the program logic using the biomedical model on different input data;
displaying a prediction list on the display of the mobile device, each list item representing one of the received prediction results and comprising at least a thumbnail-analog scale icon graphically representing said prediction result, each thumbnail-analog scale icon comprising at least:
a size-reduced version of the scale,
a size-reduced version of the background area with the prediction score, and
a size-reduced version of the pointer originating at the center of the size-reduced background area and pointing towards a location within the size-reduced scale that represents the prediction score;
upon a user's selection of one of the list items, performing the generation and the displaying of the analog scale icon, wherein the analog scale icon represents the prediction result represented by the selected list item, wherein the analog scale icon replaces the prediction list on the matrix display of the mobile device.

12. The method of claim 1, wherein the analog scale icon is displayed as an element of a graphical user interface that is free of a scroll bar and/or that does not support scrolling.

13. The method of claim 1, wherein the generation of the analog scale icon is performed by one of:
a browser executing a script element of a web page provided by a server computer; or
by a browser plug in of a browser displaying a web page provided by a server computer; or
by an application program, the application program being interoperable with a backend program hosted by the server computer, the backend program being adapted to provide the prediction result to the mobile device via a network.

14. The method of claim 1, further comprising normalizing an original prediction score generated by the program logic and using the normalized prediction score as the prediction score generated by the program logic, wherein the normalized score is normalized based on a predefined score range.

15. The method of claim 1, further comprising:
repeatedly performing, by the program logic, the generation of the prediction result for the biomedical prediction task, thereby using repeatedly updated versions of the biomedical model, and
visualizing the change of the certainty of the repeatedly updated biomedical model in the form of a moving image of the analog scale icon, wherein the size of the first and second sub-range indicators, the direction of the pointer and/or the size of the variance bar, if any, vary in the moving image over time.

16. A mobile hand-held telecommunication device comprising:
a battery for powering the mobile device;
a digital cellular network interface;
a matrix display; and
a program logic executable by the one or more processors and configured for:
receiving a prediction result via the digital cellular network interface, the prediction result having been generated for a biomedical prediction task by a predictive program logic using a biomedical model, the prediction result comprising at least:
a prediction score, the prediction score being indicative of the certainty of the prediction and being a numerical value within a score range, the score range being a predefined range of possible score values;
a first confidence interval, the first confidence interval being a first sub-interval of the score range, wherein the first confidence interval is indicative of the model-specific sub-range of score values known to have a percentage of false negative predictions below a predefined FN-percentage threshold;
a second confidence interval, the second confidence interval being a second sub-interval of the score range, wherein the second confidence interval is indicative of the model-specific sub-range of score values known to have a percentage of false positive predictions below a predefined FP-percentage threshold; and
a prediction-variance-interval, the prediction-variance-interval being indicative of a sub-range of the score range, the width of the prediction-variance-interval quantifying the amount of variation or dispersion of the prediction scores computed by program logic using the biological model;
displaying an analog scale icon on the matrix display, the analog scale icon comprising:
a background area comprising the prediction score;
an analog scale representing the score range, wherein the ends of the scale represent the maximum and minimum score values of the score range;
a pointer pointing towards a location within the scale that represents the prediction score;
a first sub-range indicator being aligned with the scale such that the size and position of the first sub-range indicator relative to the scale is indicative of the size and position of the first confidence interval within the score range;
a second sub-range indicator being aligned with the scale such that the size and position of the second sub-range indicator relative to the scale is indicative of the size and position of the second confidence interval within the score range; and
a variance bar arranged perpendicular to the pointer, the width of the variance bar correlating with and being indicative of the width of the prediction-variance-interval.

17. A system comprising the mobile device of claim 16 and a server computer, the server computer comprising:
the biomedical model;
the program logic configured to use the biomedical model for generating the prediction result;
a backend program adapted to provide the prediction result via a network to the mobile device.

* * * * *